(12) United States Patent
Hamblin et al.

(10) Patent No.: US 10,383,879 B2
(45) Date of Patent: Aug. 20, 2019

(54) COMPOUNDS

(71) Applicant: Glaxo Group Limited, Brentford, Middlesex (GB)

(72) Inventors: Julie Nicole Hamblin, Stevenage (GB); Paul Spencer Jones, Stevenage (GB); Suzanne Elaine Keeling, Stevenage (GB); Joelle Le, Stevenage (GB); Charlotte Jane Mitchell, Stevenage (GB); Nigel James Parr, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 16/280,094

(22) Filed: Feb. 20, 2019

(65) Prior Publication Data

US 2019/0175608 A1    Jun. 13, 2019

Related U.S. Application Data

(60) Continuation of application No. 15/980,778, filed on May 16, 2018, which is a continuation of application No. 15/433,010, filed on Feb. 15, 2017, now abandoned, which is a continuation of application No. 15/225,962, filed on Aug. 2, 2016, now abandoned, which is a continuation of application No. 14/722,176, filed on May 27, 2015, now abandoned, which is a continuation of application No. 14/088,505, filed on Nov. 25, 2013, now abandoned, which is a continuation of application No. 13/633,230, filed on Oct. 2, 2012, now Pat. No. 8,609,657, which is a division of application No. 12/768,775, filed on Apr. 28, 2010, now Pat. No. 8,575,162.

(60) Provisional application No. 61/174,033, filed on Apr. 30, 2009.

(51) Int. Cl.
| | |
|---|---|
| *C07D 413/14* | (2006.01) |
| *A61K 31/5377* | (2006.01) |
| *A61K 45/06* | (2006.01) |
| *A61K 31/535* | (2006.01) |
| *A61K 31/496* | (2006.01) |
| *A61K 31/497* | (2006.01) |

(52) U.S. Cl.
CPC ........ *A61K 31/5377* (2013.01); *A61K 31/496* (2013.01); *A61K 31/497* (2013.01); *A61K 31/535* (2013.01); *A61K 45/06* (2013.01); *C07D 413/14* (2013.01); *C07B 2200/13* (2013.01); *Y02A 50/409* (2018.01)

(58) Field of Classification Search
CPC .................................................. C07D 413/14
See application file for complete search history.

(56) References Cited

U.S. PATENT DOCUMENTS

| | | |
|---|---|---|
| 8,076,326 B2 | 12/2011 | Haupt et al. |
| 8,114,868 B2 | 2/2012 | Himmelsbach |
| 8,138,178 B2 | 3/2012 | Claremon et al. |
| 8,163,743 B2 | 4/2012 | Baldwin et al. |
| 8,242,111 B2 | 8/2012 | Claremon et al. |
| 8,524,751 B2 | 9/2013 | Hamblin et al. |
| 8,575,162 B2 | 11/2013 | Hamblin et al. |
| 8,580,797 B2 | 11/2013 | Hamblin et al. |
| 8,586,583 B2 | 11/2013 | Hamblin et al. |
| 8,586,590 B2 | 11/2013 | Hamblin et al. |
| 8,609,657 B2 | 12/2013 | Hamblin et al. |
| 8,735,390 B2 | 5/2014 | Hamblin et al. |
| 8,993,576 B2 | 3/2015 | Hamblin et al. |
| 9,102,668 B2 | 8/2015 | Hamblin et al. |
| 9,326,987 B2 | 5/2016 | Hamblin et al. |
| 9,353,098 B2 | 5/2016 | Hamblin et al. |
| 2004/0009968 A1 | 1/2004 | Binch et al. |
| 2004/0014802 A1 | 1/2004 | Duntruc-Rosset et al. |
| 2005/0090529 A1 | 4/2005 | McAlpine et al. |
| 2005/0288286 A1 | 12/2005 | Flynn et al. |
| 2006/0135540 A1 | 6/2006 | Lin et al. |
| 2006/0264433 A1 | 11/2006 | Backes et al. |
| 2007/0037820 A1 | 2/2007 | Edwards et al. |

(Continued)

FOREIGN PATENT DOCUMENTS

| | | |
|---|---|---|
| EP | 1679308 A1 | 7/2006 |
| WO | 1998/03487 A1 | 1/1998 |

(Continued)

OTHER PUBLICATIONS

Ameriks, et al. Small Molecule Inhibitors of Phosphoinositide 3-kinase (PI3K) delta and gamma Current Topics in Medicinal Chemistry; 2009; vol. 9(8); pp. 738-753.

(Continued)

*Primary Examiner* — Rebecca L Anderson
(74) *Attorney, Agent, or Firm* — Robert J. Smith

(57) ABSTRACT

The invention is directed to compounds of formula (I):

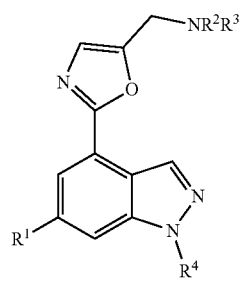

and salts thereof. The compounds of the invention are inhibitors of kinase activity, in particular PI3-kinase activity.

8 Claims, 2 Drawing Sheets

(56) References Cited

U.S. PATENT DOCUMENTS

| | | |
|---|---|---|
| 2008/0032960 A1 | 2/2008 | Knight et al. |
| 2008/0200523 A1 | 8/2008 | Murthi et al. |
| 2009/0203690 A1 | 8/2009 | Akritopoulou-Zanze et al. |
| 2010/0216792 A1 | 8/2010 | Gorgens et al. |
| 2010/0256363 A1 | 10/2010 | Xu |
| 2010/0280014 A1 | 11/2010 | Haupt et al. |
| 2010/0280029 A1 | 11/2010 | Hamblin et al. |
| 2010/0280045 A1 | 11/2010 | Hamblin et al. |
| 2010/0331320 A1 | 12/2010 | Renz et al. |
| 2011/0009402 A1 | 1/2011 | Himmelsbach |
| 2011/0015157 A1 | 1/2011 | Claremon et al. |
| 2011/0021512 A1 | 1/2011 | Claremon et al. |
| 2011/0067448 A1 | 3/2011 | Matsumoto et al. |
| 2011/0118246 A1 | 5/2011 | Baldwin et al. |
| 2011/0124635 A1 | 5/2011 | Claremon et al. |
| 2011/0178063 A1 | 7/2011 | Baldwin et al. |
| 2011/0183973 A1 | 7/2011 | Baldwin et al. |
| 2011/0263583 A1 | 10/2011 | Claremon et al. |
| 2011/0263584 A1 | 10/2011 | Claremon et al. |
| 2012/0040969 A1 | 2/2012 | Haupt et al. |
| 2012/0108579 A1 | 5/2012 | Renz et al. |
| 2012/0129854 A1 | 5/2012 | Mihara et al. |
| 2012/0178746 A1 | 7/2012 | Claremon et al. |
| 2012/0184549 A1 | 7/2012 | Himmelsbach |
| 2012/0238559 A1 | 9/2012 | Baldwin et al. |
| 2012/0238571 A1 | 9/2012 | Baldwin et al. |
| 2012/0245171 A1 | 9/2012 | Baldwin et al. |

FOREIGN PATENT DOCUMENTS

| | | |
|---|---|---|
| WO | 2002/067683 A1 | 9/2002 |
| WO | 2002/83111 A1 | 10/2002 |
| WO | 2003/000257 A1 | 1/2003 |
| WO | 2003/051847 A1 | 6/2003 |
| WO | 2003/064397 A1 | 8/2003 |
| WO | 2004/002480 A1 | 1/2004 |
| WO | 2004/014370 A1 | 2/2004 |
| WO | 2004/014881 A1 | 2/2004 |
| WO | 2004/014902 A1 | 2/2004 |
| WO | 2005/016245 A1 | 2/2005 |
| WO | 2005/075482 A1 | 8/2005 |
| WO | 2005/077345 A1 | 8/2005 |
| WO | 2005/077368 A1 | 8/2005 |
| WO | 2005/077373 A1 | 8/2005 |
| WO | 2005/082889 A1 | 9/2005 |
| WO | 2006/012226 A1 | 2/2006 |
| WO | 2006/014290 A1 | 2/2006 |
| WO | 2006/055752 A1 | 5/2006 |
| WO | 2006/060535 A2 | 6/2006 |
| WO | 2006/089076 A2 | 8/2006 |
| WO | 2006/135383 A1 | 12/2006 |
| WO | 2007/017759 A1 | 2/2007 |
| WO | 2007/021573 A1 | 2/2007 |
| WO | 2007/022371 A1 | 2/2007 |
| WO | 2007/105637 A1 | 9/2007 |
| WO | 2007/117465 A2 | 10/2007 |
| WO | 2007/126841 A2 | 11/2007 |
| WO | 2007/132171 A1 | 11/2007 |
| WO | 2008/016123 A1 | 2/2008 |
| WO | 2008/020229 A1 | 2/2008 |
| WO | 2008/024945 A1 | 2/2008 |
| WO | 2008/037477 A1 | 4/2008 |
| WO | 2008/038136 A1 | 4/2008 |
| WO | 2008/057938 A1 | 5/2008 |
| WO | 2008/090382 A1 | 7/2008 |
| WO | 2008/139161 A1 | 11/2008 |
| WO | 2009/000832 A1 | 12/2008 |
| WO | 2009/017664 A1 | 2/2009 |
| WO | 2009/134400 A1 | 11/2009 |
| WO | 2009/147187 A1 | 12/2009 |
| WO | 2009/147189 A1 | 12/2009 |
| WO | 2009/147190 A1 | 12/2009 |
| WO | 2010/011314 A1 | 1/2010 |
| WO | 2010/043315 A1 | 4/2010 |
| WO | 2010/068287 A1 | 6/2010 |
| WO | 2010/083163 A1 | 7/2010 |
| WO | 2010/102958 A1 | 9/2010 |
| WO | 2010/0125082 A1 | 11/2010 |
| WO | 2010/125134 A1 | 11/2010 |
| WO | 2010/127237 A2 | 11/2010 |
| WO | 2011/067364 A1 | 6/2011 |
| WO | 2012/032065 A1 | 3/2012 |
| WO | 2012/032067 A1 | 3/2012 |
| WO | 2012/055846 A1 | 5/2012 |
| WO | 2009/147188 A1 | 1/2014 |

OTHER PUBLICATIONS

Centers for Disease Control and Prevention. Public Health Strategic Framework for COPD Prevention. Atlanta, GA: Centers for Disease Control and Prevention; 2011.

Finan, et al., "PI3-kinase inhibition: a therapeutic target for respiratory disease." Biochemical Society Transactions; 2004; vol. 32, part 2; pp. 378-382.

Folkes, et al., "The Identification of 2-(1H-indazol-4-yl)-6-(4-methanesulfonyl-piperazin-1-ylmethyl)-4-morpholin-4-yl-thieno[3,2-d]pyrimidine (GDC-0941) as a Potent, Selective, Orally Bioavailable inhibitor of class I PI3 kinase for the treatment of cancer." Journal of Medicinal Chemistry; 2008; vol. 51(18); pp. 5522-5532.

Golub, et al., "Molecular Classification of Cancer: Class Discovery and Class Prediction by Gene Expression Monitoring"; Science; 1999; vol. 286; pp. 531-537.

Horig, et al., "From bench to clinic and back: Perspective on the 1st IQPC Translational Research Conference": Journal of Translational Medicine; 2004; vol. 2(44) ; pp. 1-8.

Jaworska, et al., SAR applicability domain, ptcl.chem.ox.ac.uk/MSDS structure activity relationship; pp. 1-8; 2004.

Lala, et al., "Role of nitric oxide in tumor progression: Lessons from experimental tumors" Cancer and Metastatis Reviews; 1998; vol. 17(1); pp. 91-106.

Schafer, et al., "Failure is an option: Learning from unsuccessful proof-of-concept trials" Drug Discovery Today; 2008; vol. 13 (21/22); pp. 913-916.

Shin, et al. "Effect of the phosphatidylinositol 3-kinase/Akt pathway on influenza A virus propagation" Journal of General Virology; 2007; vol. 88; pp. 942-950.

Verheijen, et al., "Phosphatidylinositol 3-kinase (PI3K) inhibitors as anticancer drugs" Jun. 1, 2007; Drugs of the Future; Prous Science; vol. 32(6); pp. 537-547.

Voskoglou-Nomikos, et al., "Clinical Predictive Value of the in Vitro Cell Line, Human Xenograft and Mouse Allograft Preclinical" 2003; Clinical Cancer Research; vol. 9; pp. 4227-4239.

U.S. Appl. No. 12/768,775, filed Apr. 28, 2010.
U.S. Appl. No. 12/768,777, filed Apr. 28, 2010.
U.S. Appl. No. 13/266,254, filed Oct. 26, 2011.
U.S. Appl. No. 13/254,034, filed Nov. 8, 2011.
Express Abandonment filed Jun. 11, 2012 for U.S. Appl. No. 13/266,254.
Letter Accompanying Express Abandonment filed Jun. 11, 2012 for U.S. Appl. No. 13/266,254.
Acknowledgment Receipt for Express Abandonment filed Jun. 11, 2012 for U.S. Appl. No. 13/266,254.
U.S. Appl. No. 15/028,954, filed Apr. 13, 2016.
U.S. Appl. No. 15/028,973, filed Apr. 13, 2016.

COMPOUNDS

This application is continuation application of Ser. No. 15/980,778 filed May 16, 2018, pending, which is a continuation of Ser. No. 15/433,010 filed Feb. 15, 2017, now abandoned, which is a continuation application of Ser. No. 15/225,962 filed Aug. 2, 2016, now abandoned, which is a continuation of Ser. No. 14/722,176, filed May 27, 2015, now abandoned, which is a continuation application of Ser. No. 14/088,505, filed Nov. 25, 2013, now abandoned, which is a continuation application of Ser. No. 13/633,230 filed Oct. 2, 2012, now U.S. Pat. No. 8,609,657, which is a divisional application of Ser. No. 12/768,775 filed Apr. 28, 2010, now U.S. Pat. No. 8,575,162, which claims priority to U.S. Provisional Ser. No. 61/174,033 filed Apr. 30, 2009, the disclosures of which are incorporated herein by reference in their entirety.

FIELD OF THE INVENTION

The present invention is directed to certain novel compounds which are inhibitors of kinase activity, processes for their preparation, pharmaceutical compositions comprising the compounds, and the use of the compounds or the compositions in the treatment of various disorders. More specifically, the compounds of the invention are inhibitors of the activity or function of the phosphoinositide 3'OH kinase family (hereinafter PI3-kinases), for example PI3Kδ, PI3Kα, PI3Kβ and/or PI3Kγ. Compounds which are inhibitors of the activity or function of PI3-kinases may be useful in the treatment of disorders such as respiratory diseases including asthma, chronic obstructive pulmonary disease (COPD) and idiopathic pulmonary fibrosis (IPF); viral infections including viral respiratory tract infections and viral exacerbation of respiratory diseases such as asthma and COPD; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain.

BACKGROUND OF THE INVENTION

Cellular membranes represent a large store of second messengers that can be enlisted in a variety of signal transduction pathways. In relation to function and regulation of effector enzymes in phospholipids signaling pathways, class I PI3-kinases (e.g. PI3Kdelta) generate second messengers from the membrane phospholipid pools. Class I PI3Ks convert the membrane phospholipid $PI(4,5)P_2$ into $PI(3,4,5)P_3$, which functions as a second messenger. PI and PI(4)P are also substrates of PI3K and can be phosphorylated and converted into PI3P and $PI(3,4)P_2$, respectively. In addition, these phosphoinositides can be converted into other phosphoinositides by 5'-specific and 3'-specific phosphatases. Thus, PI3K enzymatic activity results either directly or indirectly in the generation of two 3'-phosphoinositide subtypes which function as second messengers in intracellular signal transduction pathways (Trends Biochem. Sci. 22(7) p. 267-72 (1997) by Vanhaesebroeck et al.; Chem. Rev. 101(8) p. 2365-80 (2001) by Leslie et al.; Annu. Rev. Cell Dev. Biol. 17 p. 615-75 (2001) by Katso et al.; and Cell. Mol. Life Sci. 59(5) p. 761-79 (2002) by Toker). To date, eight mammalian PI3Ks have been identified, divided into three main classes (I, II, and III) on the basis of sequence homology, structure, binding partners, mode of activation, and substrate preference. In vitro, class I PI3Ks can phosphorylate phosphatidylinositol (PI), phosphatidylinositol-4-phosphate (PI4P), and phosphatidylinositol-4,5-bisphosphate $(PI(4,5)P_2)$ to produce phosphatidylinositol-3-phosphate (PI3P), phosphatidylinositol-3,4-bisphosphate $(PI(3,4)P_2)$, and phosphatidylinositol-3,4,5-trisphosphate $(PI(3,4,5)P_3)$, respectively. Class 11 PI3Ks can phosphorylate PI and PI4P. Class III PI3Ks can only phosphorylate PI (Vanhaesebroeck et al. (1997), above; Vanhaesebroeck et al. Exp. Cell Res. 253(1) p. 239-54 (1999); and Leslie et al. (2001), above).

Class I PI3K is a heterodimer consisting of a p110 catalytic subunit and a regulatory subunit, and the family is further divided into class Ia and class Ib enzymes on the basis of regulatory partners and mechanism of regulation. Class Ia enzymes consist of three distinct catalytic subunits (p110α, p110β, and p110δ) that dimerise with five distinct regulatory subunits (p85α, p55α, p50α, p85β, and p55γ), with all catalytic subunits being able to interact with all regulatory subunits to form a variety of heterodimers. Class Ia PI3K are generally activated in response to growth factor-stimulation of receptor tyrosine kinases, via interaction of the regulatory subunit SH2 domains with specific phospho-tyrosine residues of the activated receptor or adaptor proteins such as IRS-1. Small GTPases (ras as an example) are also involved in the activation of PI3K in conjunction with receptor tyrosine kinase activation. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzyme is activated in response to G-protein coupled receptor (GPCR) systems and its expression appears to be limited to leukocytes.

Scheme A: Conversion of PI(4,5)P$_2$ to PI(3,4,5)P$_3$

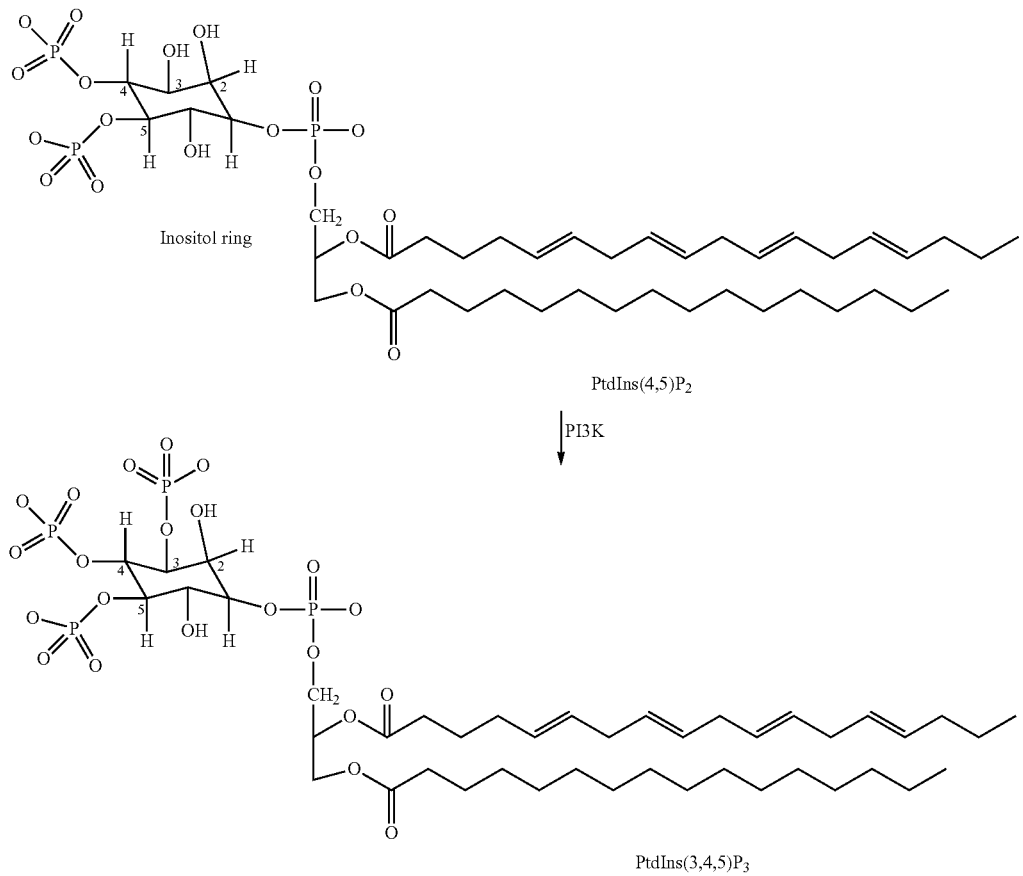

As illustrated in Scheme A above, phosphoinositide 3-kinases (PI3Ks) phosphorylate the hydroxyl of the third carbon of the inositol ring. The phosphorylation of phosphoinositides to generate PtdIns(3,4,5)P$_3$, PtdIns(3,4)P$_2$ and PtdIns(3)P, produces second messengers for a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Katso et al. (2001), above; and Mol. Med. Today 6(9) p. 347-57 (2000) by Stein et al.).

The activity of PI3-kinases responsible for generating these phosphorylated signalling products was originally identified as being associated with viral oncoproteins and growth factor receptor tyrosine kinases that phosphorylate phosphatidylinositol (PI) and its phosphorylated derivatives at the 3'-hydroxyl of the inositol ring (Panayotou et al. Trends Cell Biol. 2 p. 358-60 (1992)). However, more recent biochemical studies have revealed that class I PI3-kinases (e.g. class IA isoform PI3Kδ) are dual-specific kinase enzymes, meaning they display both lipid kinase (phosphorylation of phosphoinositides) as well as protein kinase activity, which have been shown to be capable of phosphorylation of other protein as substrates, including auto-phosphorylation as an intramolecular regulatory mechanism (EMBO J. 18(5) p. 1292-302 (1999) by Vanhaesebroeck et al.). Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

PI3-kinase activation, is believed to be involved in a wide range of cellular responses including cell growth, differentiation, and apoptosis (Parker, Current Biology 5(6) p. 577-79 (1995); and Yao et al. Science 267(5206) p. 2003-06 (1995)). PI3-kinase appears to be involved in a number of aspects of leukocyte activation. A p85-associated PI3-kinase has been shown to physically associate with the cytoplasmic domain of CD28, which is an important costimulatory molecule for the activation of T-cells in response to antigen (Pages et al. Nature 369 p. 327-29 (1994); and Rudd, Immunity 4 p. 527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al. Science 251(4991) p. 313-16 (1991)).

PI3Kγ has been identified as a mediator of G beta-gamma-dependent regulation of JNK activity, and G beta-gamma are subunits of heterotrimeric G proteins (Lopez-llasaca et al. J. Biol. Chem. 273(5) p. 2505-8 (1998)). Recently, (Laffargue et al. Immunity 16(3) p. 441-51 (2002)) it has been described that PI3Kγ relays inflammatory signals through various G(i)-coupled receptors and is central to mast cell function, stimuli in the context of leukocytes, and immunology including cytokines, chemokines, adenosines, antibodies, integrins, aggregation factors, growth factors, viruses or hormones for example (J. Cell Sci. 114 (Pt 16) p. 2903-10 (2001) by Lawlor et al.; Laffargue et al. (2002), above; and Curr. Opinion Cell Biol. 14(2) p. 203-13 (2002) by Stephens et al.).

Specific inhibitors against individual members of a family of enzymes provide invaluable tools for deciphering functions of each enzyme. Two compounds, LY294002 and wortmannin (hereinafter), have been widely used as PI3-kinase inhibitors. These compounds are non-specific PI3K inhibitors, as they do not distinguish among the four members of Class I PI3-kinases. For example, the $IC_{50}$ values of wortmannin against each of the various Class I PI3-kinases are in the range of 1-10 nM. Similarly, the $IC_{50}$ values for LY294002 against each of these PI3-kinases is about 15-20 µM (Fruman et al. Ann. Rev. Biochem. 67 p. 481-507 (1998)), also 5-10 microM on CK2 protein kinase and some inhibitory activity on phospholipases. Wortmannin is a fungal metabolite which irreversibly inhibits PI3K activity by binding covalently to the catalytic domain of this enzyme. Inhibition of PI3K activity by wortmannin eliminates subsequent cellular response to the extracellular factor. For example, neutrophils respond to the chemokine fMet-Leu-Phe (fMLP) by stimulating PI3K and synthesizing PtdIns (3, 4, 5)$P_3$. This synthesis correlates with activation of the respiratory burst involved in neutrophil destruction of invading microorganisms. Treatment of neutrophils with wortmannin prevents the fMLP-induced respiratory burst response (Thelen et al. Proc. Natl. Acad. Sci. USA 91 p. 4960-64 (1994)). Indeed, these experiments with wortmannin, as well as other experimental evidence, show that PI3K activity in cells of hematopoietic lineage, particularly neutrophils, monocytes, and other types of leukocytes, is involved in many of the non-memory immune response associated with acute and chronic inflammation.

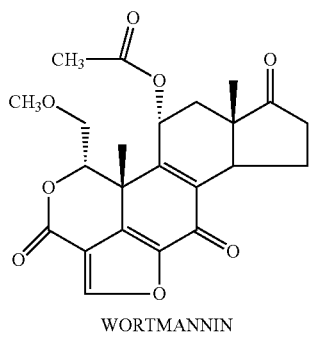

WORTMANNIN

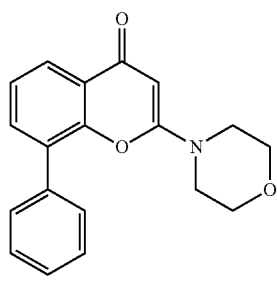

LY294002

Based on studies using wortmannin, there is evidence that PI3-kinase function is also required for some aspects of leukocyte signaling through G-protein coupled receptors (Thelen et al. (1994), above). Moreover, it has been shown that wortmannin and LY294002 block neutrophil migration and superoxide release.

It is now well understood that deregulation of oncogenes and tumour suppressor genes contributes to the formation of malignant tumours, for example by way of increased cell growth and proliferation or increased cell survival. It is also now known that signaling pathways mediated by the PI3K family have a central role in a number of cell processes including proliferation and survival, and deregulation of these pathways is a causative factor a wide spectrum of human cancers and other diseases (Katso et al. Annual Rev. Cell Dev. Biol. (2001) 17 p. 615-675 and Foster et al. J. Cell Science (2003) 116(15) p. 3037-3040). PI3K effector proteins initiate signalling pathways and networks by translocating to the plasma membrane through a conserved Pleckstrin Homology (PH) domain, which specifically interacts with PtdIns(3,4,5)P3 (Vanhaesebroeck et al. Annu. Rev. Biochem. (2001) 70 p. 535-602). The effector proteins signalling through PtdIns(3,4,5)P3 and PH domains include Serine/Threonine (Ser/Thr) kinases, Tyrosine kinases, Rac or Arf GEFs (Guanine nucleotide exchange factors) and Arf GAPs (GTPase activating proteins).

In B and T cells PI3Ks have an important role through activation of the Tec family of protein tyrosine kinases which include Bruton's tyrosine kinase (BTK) in B cells and Interleukin-2-inducible T-cell kinase (ITK) in T cells. Upon PI3K activation, BTK or ITK translocate to the plasma membrane where they are subsequently phosphorylated by Src kinases. One of the major targets of activated ITK is phospholipase C-gamma (PLCγ1), which hydrolyses PtdIns (4,5)P2 into Ins(3,4,5)P3 and initiates an intracellular increase in calcium levels and diacylglycerol (DAG) which can activate Protein Kinases C in activated T cells.

Unlike the Class IA p110α and p110β, p110δ is expressed in a tissue restricted fashion. Its high expression level in lymphocytes and lymphoid tissues suggests a role in PI3K-mediated signalling in the immune system. The p110δ kinase dead knock-in mice are also viable and their phenotype is restricted to defects in immune signalling (Okkenhaug et al. Science (2002) 297 p. 1031-4). These transgenic mice have offered insight into the function of PI3Kδ in B-cell and T-cell signalling. In particular, p110δ is required for PtdIns(3,4,5)P3 formation downstream of CD28 and/or T cell Receptor (TCR) signalling. A key effect of PI3K signalling downstream of TCR is the activation of Akt, which phosphorylates anti-apoptotic factors as well as various transcription factors for cytokine production. As a consequence, T cells with inactive p110δ have defects in proliferation and Th1 and Th2 cytokine secretion. Activation of T cells through CD28 lowers the threshold for TCR activation by antigen and increases the magnitude and duration of the proliferative response. These effects are mediated by the PI3Kδ-dependent increase in the transcription of a number of genes including IL2, an important T cell growth factor.

Therefore, PI3K inhibitors are anticipated to provide therapeutic benefit via its role in modulating T-cell mediated inflammatory responses associated to respiratory diseases such as asthma, COPD and cystic fibrosis. In addition, there is indication that T-cell directed therapies may provide corticosteroid sparing properties (Alexander et al. Lancet (1992) 339 p. 324-8) suggesting that it may provide a useful therapy either as a standalone or in combination with inhaled or oral glucocorticosteroids in respiratory diseases. A PI3K inhibitor might also be used alongside other conventional therapies such as a long acting beta-agonists (LABA) in asthma.

In the vasculature, PI3Kδ is expressed by endothelial cells and participates in neutrophil trafficking by modulating the proadhesive state of these cells in response to TNFalpha (Puri et al. Blood (2004) 103(9) p. 3448-56.). A role for PI3Kδ in TNFalpha-induced signalling of endothelial cells is demonstrated by the pharmacological inhibition of Akt phosphorylation and PDK1 activity. In addition, PI3Kδ is implicated in vascular permeability and airway tissue edema through the VEGF pathway (Lee et al. J. Allergy Clin. Immunol. (2006) 118(2) p. 403-9). These observations suggest additional benefits of PI3Kδ inhibition in asthma by the combined reduction of leukocyte extravasation and vascular permeability associated with asthma. In addition, PI3Kδ activity is required for mast cell function both in vitro and in vivo (Ali et al. Nature (2004) 431 p. 1007-11; and Ali et al. J. Immunol. (2008) 180(4) p. 2538-44) further suggesting that PI3K inhibition should be of therapeutical benefit for allergic indications such asthma, allergic rhinitis and atopic dermatitis.

The role of PI3Kδ in B cell proliferation, antibody secretion, B-cell antigen and IL-4 receptor signalling, B-cell antigen presenting function is also well established Okkenhaug et al. (2002), above; Al-Alwan et al. J. Immunol. (2007) 178(4) p. 2328-35; and Bilancio et al. Blood (2006) 107(2) p. 642-50) and indicates a role in autoimmune diseases such as rheumatoid arthritis or systemic lupus erythematosus. Therefore PI3K inhibitors may also be of benefit for these indications.

Pharmacological inhibition of PI3Kδ inhibits fMLP-dependent neutrophil chemotaxis on an ICAM coated agarose matrix integrin-dependent biased system (Sadhu et al., J. Immunol. (2003) 170(5) p. 2647-54.). Inhibition of PI3Kδ regulates neutrophil activation, adhesion and migration without affecting neutrophil mediated phagocytosis and bactericidal activity over *Staphylococcus aureus* (Sadhu et al. Biochem. Biophys. Res. Commun. (2003) 308(4) p. 764-9). Overall, the data suggest that PI3Kδ inhibition should not globally inhibit neutrophil functions required for innate immune defense. PI3Kδ's role in neutrophils offers further scope for treating inflammatory diseases involving tissue remodeling such as COPD or rheumatoid arthritis.

In addition, there is also good evidence that class Ia PI3K enzymes also contribute to tumourigenesis in a wide variety of human cancers, either directly or indirectly (Vivanco and Sawyers, Nature Reviews Cancer (2002) 2(7) p. 489-501). For example, inhibition of PI3Kδ may have a therapeutic role for the treatment of malignant haematological disorders such as acute myeloid leukaemia (Billottet et al. Oncogene (2006) 25(50) p. 6648-59). Moreover, activating mutations within p110α (PIK3CA gene) have been associated with various other tumors such as those of the colon and of the breast and lung (Samuels et al. Science (2004) 304(5670) p. 554).

It has also been shown that PI3K is involved in the establishment of central sensitization in painful inflammatory conditions (Pezet et al. The J. of Neuroscience (2008) 28 (16) p. 4261-4270).

A wide variety of retroviruses and DNA based viruses activate the PI3K pathway as a way of preventing host cell death during viral infection and ultimately exploiting the host cell synthesis machinery for its replication (Virology 344(1) p. 131-8 (2006) by Vogt et al.; and Nat. Rev. Microbiol. 6(4) p. 265-75 (2008) by Buchkovich et al.). Therefore PI3K inhibitors may have anti-viral properties in addition to more established oncolytic and anti-inflammatory indications. These antiviral effects raise interesting prospects in viral induced inflammatory exacerbations. For example, the common cold human rhinovirus (HRV) is responsible for more than 50% of respiratory tract infections but complications of these infections can be significant in certain populations. This is particularly the case in respiratory diseases such as asthma or chronic obstruction pulmonary disease (COPD). Rhinoviral infection of epithelial cells leads to a PI3K dependent cytokine and chemokine secretion (J. Biol. Chem. (2005) 280(44) p. 36952 by Newcomb et al.). This inflammatory response correlates with worsening of respiratory symptoms during infection. Therefore PI3K inhibitors may dampen an exaggerated immune response to an otherwise benign virus. The majority of HRV strains infect bronchial epithelial cells by initially binding to the ICAM-1 receptor. The HRV-ICAM-1 complex is then further internalised by endocytosis and it has been shown that this event requires PI3K activity (J. Immunol. (2008) 180(2) p. 870-880 by Lau et al.). Therefore, PI3K inhibitors may also block viral infections by inhibiting viral entry into host cells.

PI3K inhibitors may be useful in reducing other types of respiratory infections including the fungal infection aspergillosis (Mucosal Immunol. (2010) 3(2) p. 193-205 by Bonifazi et al.). In addition, PI3Kδ deficient mice are more resistant towards infections by the protozoan parasite *Leishmania major* (J. Immunol. (2009) 183(3) p. 1921-1933 by Liu et al.). Taken with effects on viral infections, these reports suggest that PI3K inhibitors may be useful for the treatment of a wide variety of infections.

PI3K inhibition has also been shown to promote regulatory T cell differentiation (Proc. Natl. Acad. Sci. USA (2008) 105(22) p. 7797-7802 by Sauer et al.) suggesting that PI3K inhibitors may serve therapeutic purposes in auto-immune or allergic indications by inducing immuno-tolerance towards self antigen or allergen. Recently the PI3Kδ isoform has also been linked to smoke induced glucocorticoid insensitivity (Am. J. Respir. Crit. Care Med. (2009) 179(7) p. 542-548 by Marwick et al.). This observation suggests that COPD patients, which otherwise respond poorly to corticosteroids, may benefit from the combination of a PI3K inhibitor with a corticosteroid.

PI3K has also been involved in other respiratory conditions such as idiopathic pulmonary fibrosis (IPF). IPF is a fibrotic disease with progressive decline of lung function and increased mortality due to respiratory failure. In IPF, circulating fibrocytes are directed to the lung via the chemokine receptor CXCR4. PI3K is required for both signalling and expression of CXCR4 (Int. J. Biochem. and Cell Biol. (2009) 41 p. 1708-1718 by Mehrad et al.). Therefore, by reducing CXCR4 expression and blocking its effector function, a PI3K inhibitor should inhibit the recruitment of fibrocytes to the lung and consequently slow down the fibrotic process underlying IPF, a disease with high unmet need.

Attempts have been made to prepare compounds which inhibit PI3-kinase activity and a number of such compounds have been disclosed in the art. However, in view of the number of pathological responses which are mediated by PI3-kinases, there remains a continuing need for inhibitors of PI3-kinase which can be used in the treatment of a variety of conditions.

The present inventors have discovered novel compounds which are inhibitors of kinase activity, in particular PI3-kinase activity. Compounds which are PI3-kinase inhibitors may be useful in the treatment of disorders associated with inappropriate kinase activity, in particular inappropriate PI3-kinase activity, for example in the treatment and prevention of disorders mediated by PI3-kinase mechanisms. Such disorders include respiratory diseases including asthma, chronic obstructive pulmonary disease (COPD) and idiopathic pulmonary fibrosis (IPF); viral infections including viral respiratory tract infections and viral exacerbation of respiratory diseases such as asthma and COPD; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain.

In one embodiment, compounds of the invention may show selectivity for PI3-kinases over other kinases.

In another embodiment, compounds of the invention may be potent inhibitors of PI3Kδ.

In a further embodiment, compounds of the invention may show selectivity for PI3Kδ over other PI3-kinases.

SUMMARY OF THE INVENTION

The invention is directed to certain novel compounds. Specifically, the invention is directed to compounds of formula (I)

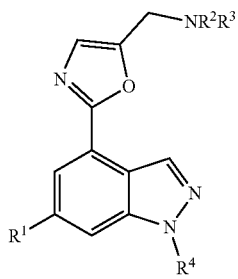

wherein $R^1$, $R^2$, $R^3$ and $R^4$ are as defined below, and salts thereof.

The compounds are inhibitors of kinase activity, in particular PI3-kinase activity. Compounds which are PI3-kinase inhibitors may be useful in the treatment of disorders associated with inappropriate PI3-kinase activity, such as asthma and chronic obstructive pulmonary disease (COPD). Accordingly, the invention is further directed to pharmaceutical compositions comprising a compound of formula (I) or a pharmaceutically acceptable salt thereof. The invention is still further directed to methods of inhibiting PI3-kinase activity and treatment of disorders associated therewith using a compound of formula (I) or a pharmaceutically acceptable salt thereof, or a pharmaceutical composition comprising a compound of formula (I) or a pharmaceutically acceptable salt thereof. The invention is yet further directed towards processes for the preparation of the compounds of the invention.

DETAILED DESCRIPTION OF THE INVENTION

Figure 1:
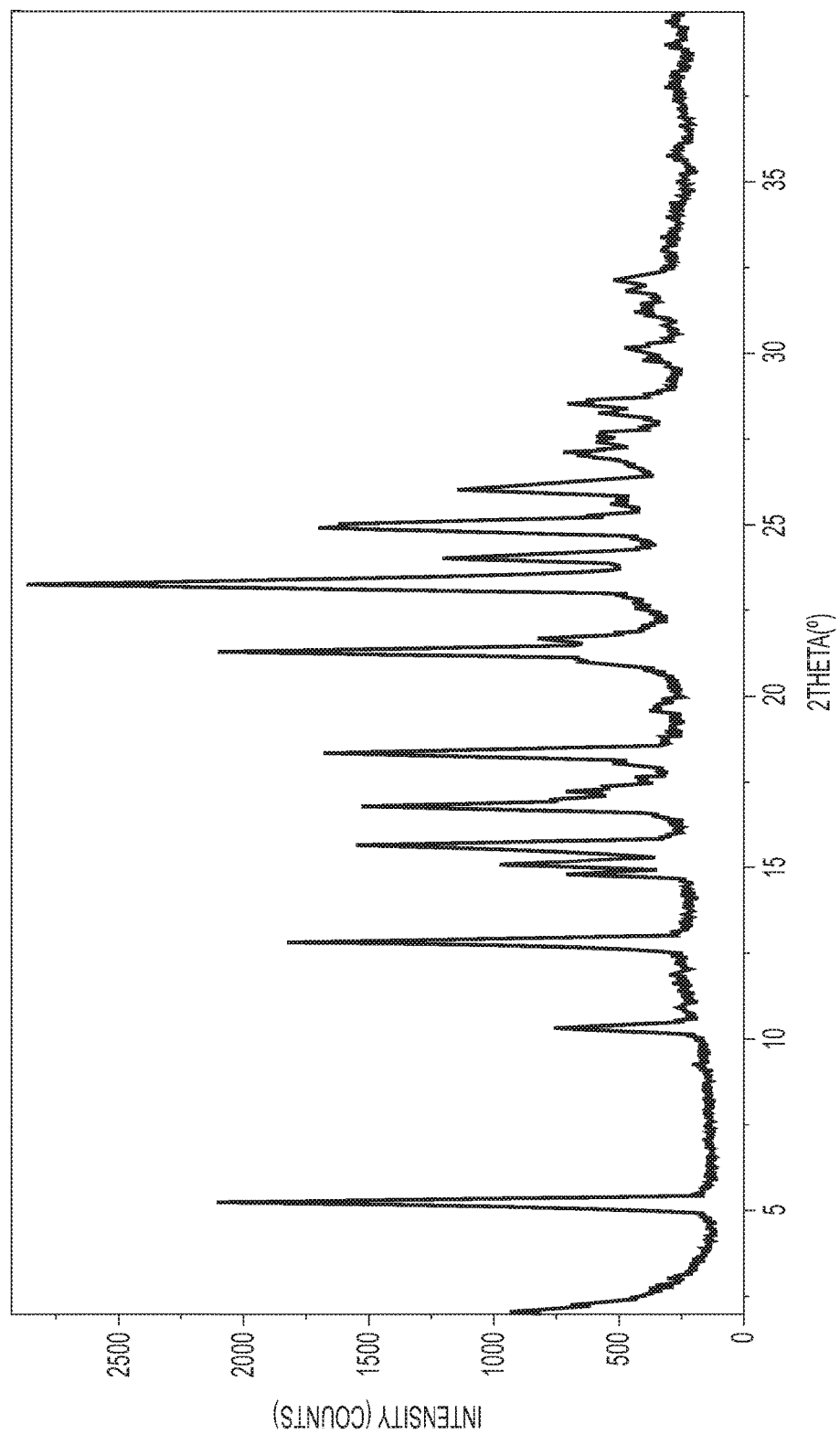
FIG. 1 shows the X-ray powder diffraction (XRPD) data for Example 10.

In one embodiment, the invention is directed to compounds of formula (I)

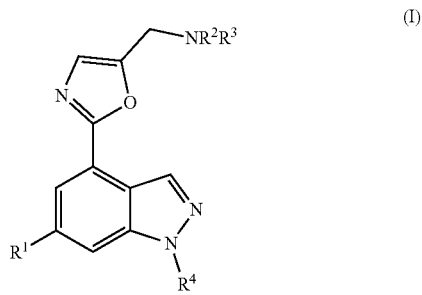

wherein $R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo, —CN or —NHSO$_2$R$^5$, or pyridinyl optionally substituted by one or two substituents independently selected from $C_{1-6}$alkyl, —OR$^6$, halo and —NHSO$_2$R$^7$;

$R^2$ and $R^3$, together with the nitrogen atom to which they are attached, are linked to form a 6- or 7-membered heterocyclyl wherein the 6- or 7-membered heterocyclyl optionally contains an oxygen atom or a further nitrogen atom and is optionally substituted by one or two substituents independently selected from $C_{1-6}$alkyl;

$R^4$ is hydrogen or methyl;

$R^6$ is hydrogen or $C_{1-4}$alkyl; and $R^5$ and $R^7$ are each independently $C_{1-6}$alkyl, or phenyl optionally substituted by one or two substituents independently selected from halo;

and salts thereof (hereinafter "compounds of the invention").

In one embodiment, $R^1$ is 9-membered bicyclic heteroaryl wherein the 9-membered bicyclic heteroaryl contains one or two nitrogen atoms, or pyridinyl optionally substituted by one or two substituents independently selected from —OR$^6$ and —NHSO$_2$R$^7$. In another embodiment, $R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo, —CN or —NHSO$_2$R$^5$. In another embodiment, $R^1$ is 9- or 10-membered bicyclic heteroaryl wherein the 9- or 10-membered bicyclic heteroaryl contains one or two nitrogen atoms and is optionally substituted by $C_{1-6}$alkyl or halo. In another embodiment, $R^1$ is 9-membered bicyclic heteroaryl wherein the 9-membered bicyclic heteroaryl contains one or two nitrogen atoms. In another embodiment, $R^1$ is indolyl, for example 1H-indol-4-yl. In another embodiment, $R^1$ is pyridinyl optionally substituted by one or two substituents independently selected from $C_{1-6}$alkyl, —OR$^6$, halo and —NHSO$_2$R$^7$. In another embodiment, R$^1$ is pyridinyl optionally substituted by one or two substituents independently selected from —OR$^6$ and —NHSO$_2$R$^7$. In a further embodiment, R$^1$ is pyridinyl substituted by —OR$^6$ and —NHSO$_2$R$^7$.

In one embodiment, R$^2$ and R$^3$, together with the nitrogen atom to which they are attached, are linked to form a 6-membered heterocyclyl wherein the 6-membered heterocyclyl optionally contains an oxygen atom or a further nitrogen atom and is optionally substituted by one or two substituents independently selected from $C_{1-6}$alkyl. In another embodiment, R$^2$ and R$^3$, together with the nitrogen atom to which they are attached, are linked to form a 6-membered heterocyclyl wherein the 6-membered heterocyclyl optionally contains an oxygen atom or a further nitrogen atom and is substituted by one or two substituents independently selected from $C_{1-4}$alkyl, for example methyl. In another embodiment, R$^2$ and R$^3$, together with the nitrogen atom to which they are attached, are linked to form a 6-membered heterocyclyl wherein the 6-membered heterocyclyl contains an oxygen atom and is optionally substituted by one or two substituents independently selected from $C_{1-4}$alkyl, for example methyl. In another embodiment, R$^2$ and R$^3$, together with the nitrogen atom to which they are attached, are linked to form a 6-membered heterocyclyl wherein the 6-membered heterocyclyl contains an oxygen atom and is substituted by one or two substituents independently selected from $C_{1-6}$alkyl. In another embodiment, R$^2$ and R$^3$, together with the nitrogen atom to which they are attached, are linked to form a 6-membered heterocyclyl wherein the 6-membered heterocyclyl contains a further nitrogen atom and is optionally substituted by $C_{1-4}$alkyl, for example isopropyl. In a further embodiment, R$^2$ and R$^3$, together with the nitrogen atom to which they are attached, are linked to form a 6-membered heterocyclyl wherein the 6-membered heterocyclyl contains a further nitrogen atom and is substituted by $C_{1-4}$alkyl, for example isopropyl.

In one embodiment, R$^4$ is hydrogen.
In one embodiment, R$^5$ is $C_{1-4}$alkyl such as methyl.
In one embodiment, R$^6$ is $C_{1-4}$alkyl such as methyl.
In one embodiment, R$^7$ is $C_{1-6}$alkyl. In another embodiment, R$^7$ is $C_{1-4}$alkyl such as methyl. In a further embodiment, R$^7$ is phenyl optionally substituted by one or two substituents independently selected from halo, for example fluoro.

It is to be understood that the present invention covers all combinations of substituent groups described hereinabove.

In one embodiment, the invention is directed to compounds of formula (IA)

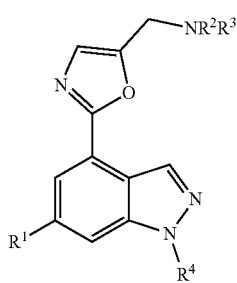

(IA)

wherein
R$^1$ is pyridinyl optionally substituted by one or two substituents independently selected from —OR$^6$ and —NHSO$_2$R$^7$;
R$^2$ and R$^3$, together with the nitrogen atom to which they are attached, are linked to form a 6-membered heterocyclyl wherein the 6-membered heterocyclyl contains an oxygen atom and is optionally substituted by one or two substituents independently selected from $C_{1-4}$alkyl;
R$^4$ is hydrogen;
R$^6$ is $C_{1-4}$alkyl; and
R$^7$ is $C_{1-4}$alkyl;
and salts thereof.

In a further embodiment, the invention is directed to compounds of formula (IB)

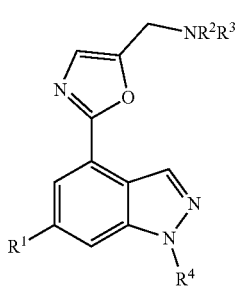

(IA)

wherein
R$^1$ is indolyl;
R$^2$ and R$^3$, together with the nitrogen atom to which they are attached, are linked to form a 6-membered heterocyclyl wherein the 6-membered heterocyclyl contains a further nitrogen atom and is optionally substituted by $C_{1-4}$alkyl; and
R$^4$ is hydrogen;
and salts thereof.

Compounds of the invention include the compounds of Examples 1 to 9 and salts thereof.

In one embodiment, the compound of the invention is:
N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide;
N-[5-[4-(5-{[4-(1-methylethyl)-1-piperazinyl]methyl}-1,3-oxazol-2-yl)-1H-indazol-6-yl]-2-(methyloxy)-3-pyridinyl]methanesulfonamide;
N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]-2,4-difluorobenzenesulfonamide;
2,4-difluoro-N-[5-[4-(5-{[4-(1-methylethyl)-1-piperazinyl]methyl}-1,3-oxazol-2-yl)-1H-indazol-6-yl]-2-(methyloxy)-3-pyridinyl]penzenesulfonamide;
4-(5-{[(2R,6S)-2,6-dimethyl-4-morpholinyl]methyl}-1,3-oxazol-2-yl)-6-(1H-indol-4-yl)-1H-indazole;
6-(1H-indol-4-yl)-4-(5-{[4-(1-methylethyl)-1-piperazinyl]methyl}-1,3-oxazol-2-yl)-1H-indazole;
6-(1H-indol-4-yl)-4-[5-(4-morpholinylmethyl)-1,3-oxazol-2-yl]-1H-indazole;
N-[5-[4-(5-{[(2R,6R)-2,6-dimethyl-4-morpholinyl]methyl}-1,3-oxazol-2-yl)-1H-indazol-6-yl]-2-(methyloxy)-3-pyridinyl]methanesulfonamide;
6-(1H-indol-4-yl)-4-[5-(1-piperazinylmethyl)-1,3-oxazol-2-yl]-1H-indazole; or a salt thereof.

In another embodiment, the compound of the invention is:
N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide;

N-[5-[4-(5-{[4-(1-methylethyl)-1-piperazinyl]methyl}-1,3-oxazol-2-yl)-1H-indazol-6-yl]-2-(methyloxy)-3-pyridinyl]methanesulfonamide;

N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]-2,4-difluorobenzenesulfonamide;

2,4-difluoro-N-[5-[4-(5-{[4-(1-methylethyl)-1-piperazinyl]methyl}-1,3-oxazol-2-yl)-1H-indazol-6-yl]-2-(methyloxy)-3-pyridinypenzenesulfonamide;

4-(5-{[(2R,6S)-2,6-dimethyl-4-morpholinyl]methyl}-1,3-oxazol-2-yl)-6-(1H-indol-4-yl)-1H-indazole;

6-(1H-indol-4-yl)-4-(5-{[4-(1-methylethyl)-1-piperazinyl]methyl}-1,3-oxazol-2-yl)-1H-indazole;

6-(1H-indol-4-yl)-4-[5-(4-morpholinylmethyl)-1,3-oxazol-2-yl]-1H-indazole;

or a salt thereof.

In another embodiment, the compound of the invention is:
N-[5-[4-(5-{[2,6-dimethyl-4-morpholinyl]methyl}-1,3-oxazol-2-yl)-1H-indazol-6-yl]-2-(methyloxy)-3-pyridinyl]methanesulfonamide;

or a salt thereof.

In another embodiment, the compound of the invention is:
N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide;

or a salt thereof.

In another embodiment, the compound of the invention is:
N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (R)-mandelate.

In another embodiment, the compound of the invention is:
N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide.

In another embodiment, the compound of the invention is:
6-(1H-indol-4-yl)-4-(5-{[4-(1-methylethyl)-1-piperazinyl]methyl}-1,3-oxazol-2-yl)-1H-indazole;

or a salt thereof.

In another embodiment, the compound of the invention is:
6-(1H-indol-4-yl)-4-(5-{[4-(1-methylethyl)-1-piperazinyl]methyl}-1,3-oxazol-2-yl)-1H-indazole hydrochloride.

In a further embodiment, the compound of the invention is:
6-(1H-indol-4-yl)-4-(5-{[4-(1-methylethyl)-1-piperazinyl]methyl}-1,3-oxazol-2-yl)-1H-indazole.

Terms and Definitions

"Alkyl" refers to a saturated hydrocarbon chain having the specified number of member atoms. For example, $C_{1-6}$alkyl refers to an alkyl group having from 1 to 6 member atoms, for example 1 to 4 member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

"Cycloalkyl" refers to a saturated hydrocarbon ring having the specified number of member atoms. Cycloalkyl groups are monocyclic ring systems. For example, $C_{3-6}$cycloalkyl refers to a cycloalkyl group having from 3 to 6 member atoms. In one embodiment, the cycloalkyl groups have 3 or 4 member atoms. In a further embodiment, the cycloalkyl groups have 5 or 6 member atoms. Cycloalkyl includes cyclopropyl, cyclobutyl, cyclopentyl, and cyclohexyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" (or "half-lives") refers to the time required for half of a quantity of a substance to be converted to another chemically distinct species in vitro or in vivo.

"Halo" refers to the halogen radical fluoro, chloro, bromo, or iodo.

"Heteroaryl", unless otherwise defined, refers to an aromatic group containing from 1 to 3 heteroatoms as member atoms. Heteroaryl groups containing more than one heteroatom may contain different heteroatoms. Heteroaryl groups may be optionally substituted as defined herein. The heteroaryl groups herein are fused bicyclic ring systems. The bicyclic heteroaryl rings have 9 or 10 member atoms. Bicyclic heteroaryl includes indolyl, isoindolyl, indolizinyl, benzofuranyl, isobenzofuranyl, indazolyl, benzimidazolyl, pyrrolopyridinyl, pyrazolopyridinyl, pyrrolopyrimidinyl, quinolyl, isoquinolinyl, quinoxalinyl, quinazolinyl, cinnolinyl, benzopyranyl, benzoxazolyl, furopyridinyl and naphthridinyl.

"Heteroatom" refers to a nitrogen, sulphur, or oxygen atom.

"Heterocyclyl", unless otherwise defined, refers to a saturated or unsaturated ring containing 1 or 2 heteroatoms as member atoms in the ring. However, heterocyclyl rings are not aromatic. In certain embodiments, heterocyclyl is saturated. In other embodiments, heterocyclyl is unsaturated but not aromatic. Heterocyclyl groups containing more than one heteroatom may contain different heteroatoms. Heterocyclyl groups may be optionally substituted with one or more substituents as defined herein. The heterocyclyl groups herein are monocyclic ring systems having 6 or 7 member atoms. Monocyclic heterocyclyl includes piperidinyl, piperazinyl, morpholinyl and hexahydro-1,4-oxazepinyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as heteroaryl, may be unsubstituted or substituted with one or more substituents as defined herein.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, salts, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

DCM Dichloromethane
DMF Dimethylformamide
DMPU 1,3-Dimethyl-3,4,5,6-tetrahydro-2-(1H)-pyrimidinone
DMSO Dimethylsulfoxide
EtOAc Ethyl acetate
g Grams
h hour(s)
HPLC High performance liquid chromatography
LCMS Liquid chromatography mass spectroscopy
L Liter
M Molar
MDAP Mass directed automated preparative HPLC
Me Methyl
MeCN Acetonitrile
MeOH Methanol
mg Milligrams
mins Minutes
ml Milliliters
mmol Millimoles
Rt Retention time
RT Room temperature
SCX Strong Cation Exchange
SPE Solid Phase Extraction
TFA Trifluoroacetic acid
THF Tetrahydrofuran
UPLC Ultra high performance liquid chromatography
UV Ultraviolet All references to brine are to a saturated aqueous solution of NaCl.

Included within the scope of the "compounds of the invention" are all solvates (including hydrates), complexes, polymorphs, prodrugs, radiolabelled derivatives, stereoisomers and optical isomers of the compounds of formula (I) and salts thereof.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs". The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

In one aspect, the present invention provides N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide or a salt thereof in crystalline form.

In one embodiment, the present invention provides N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide in crystalline form.

In another embodiment, the present invention provides crystalline N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD (X-ray powder diffraction) pattern having peaks (° 2θ) at about 4.5, about 11.7 and/or about 12.9.

In another embodiment, the present invention provides crystalline N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern comprising peaks substantially as set out in Table 2.

Figure 2:
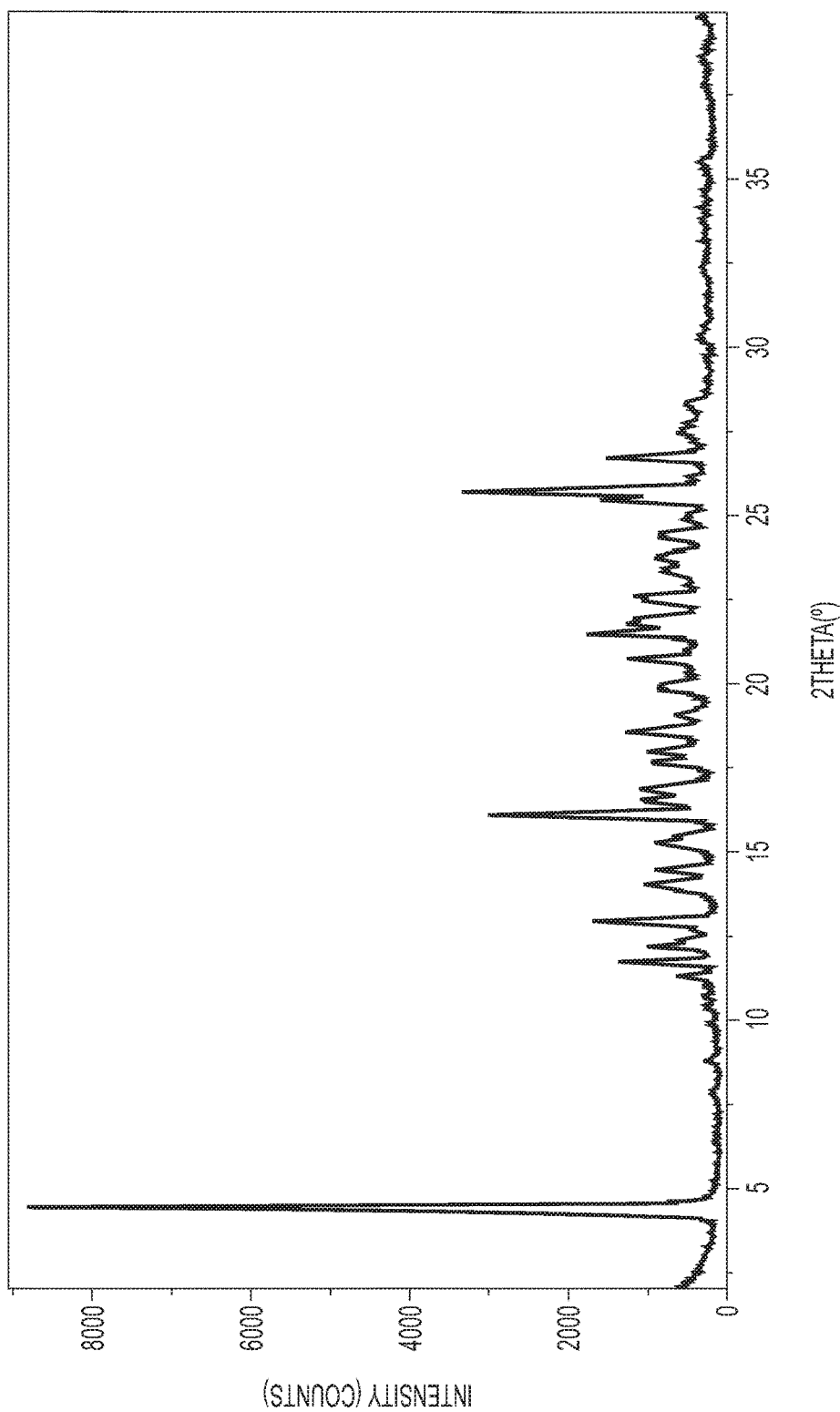
FIG. 2 shows the X-ray powder diffraction (XRPD) data for Example 1.

In another embodiment, the present invention provides crystalline N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern substantially in accordance with FIG. 2.

In a further aspect, the present invention provides 6-(1H-indol-4-yl)-4-(5-{[4-(1-methylethyl)-1-piperazinyl]methyl}-1,3-oxazol-2-yl)-1H-indazole or a salt thereof in crystalline form.

In one embodiment, the present invention provides 6-(1H-indol-4-yl)-4-(5-{[4-(1-methylethyl)-1-piperazinyl]methyl}-1,3-oxazol-2-yl)-1H-indazole hydrochloride in crystalline form.

In another embodiment, the present invention provides crystalline 6-(1H-indol-4-yl)-4-(5-{[4-(1-methylethyl)-1-piperazinyl]methyl}-1,3-oxazol-2-yl)-1H-indazole hydrochloride characterised in that it provides an XRPD (X-ray powder diffraction) pattern having peaks (° 2θ) at about 5.2, about 10.3 and/or about 12.8.

In another embodiment, the present invention provides crystalline 6-(1H-indol-4-yl)-4-(5-{[4-(1-methylethyl)-1-piperazinyl]methyl}-1,3-oxazol-2-yl)-1H-indazole hydrochloride characterised in that it provides an XRPD pattern comprising peaks substantially as set out in Table 1.

In a further embodiment, the present invention provides crystalline 6-(1H-indol-4-yl)-4-(5-{[4-(1-methylethyl)-1-piperazinyl]methyl}-1,3-oxazol-2-yl)-1H-indazole hydrochloride characterised in that it provides an XRPD pattern substantially in accordance with Figure When it is indicated herein that there is a peak in an XRPD pattern at a given value, it is typically meant that the peak is within ±0.2 of the value quoted.

The invention also includes isotopically-labelled compounds, which are identical to the compounds of formula (I) and salts thereof, but for the fact that one or more atoms are replaced by an atom having an atomic mass or mass number different from the atomic mass or mass number most commonly found in nature. Examples of isotopes that can be incorporated into the compounds of the invention include isotopes of hydrogen, carbon, nitrogen, oxygen and fluorine, such as $^2$H, $^3$H, $^{11}$C, $^{14}$C and $^{18}$F.

The compounds according to formula (I) may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in formula (I), or in any chemical structure illustrated herein, is not specified the structure is intended to encompass any stereoisomer and all mixtures thereof. Thus, compounds according to formula (I) containing one or more chiral center may be used as racemic mixtures, enantiomerically enriched mixtures, or as enantiomerically pure individual stereoisomers.

Individual stereoisomers of a compound according to formula (I) which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to formula (I) may also contain centers of geometric asymmetry. Where the stereochemistry of a center of geometric asymmetry present in formula (I), or in any chemical structure illustrated herein, is not specified, the structure is intended to encompass the trans geometric isomer, the cis geometric isomer, and all mixtures thereof. Likewise, all tautomeric forms are also included in formula (I) whether such tautomers exist in equilibrium or predominately in one form.

It is to be understood that the references herein to compounds of formula (I) and salts thereof covers the compounds of formula (I) as free acids or free bases, or as salts thereof, for example as pharmaceutically acceptable salts thereof. Thus, in one embodiment, the invention is directed to compounds of formula (I) as the free acid or free base. In another embodiment, the invention is directed to compounds of formula (I) and salts thereof. In a further embodiment, the invention is directed to compounds of formula (I) and pharmaceutically acceptable salts thereof.

The skilled artisan will appreciate that pharmaceutically acceptable salts of the compounds according to formula (I) may be prepared. Indeed, in certain embodiments of the invention, pharmaceutically acceptable salts of the compounds according to formula (I) may be preferred over the respective free base or free acid because such salts may impart greater stability or solubility to the molecule thereby facilitating formulation into a dosage form. Accordingly, the invention is further directed to compounds of formula (I) and pharmaceutically acceptable salts thereof.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form, or a non-pharmaceutically acceptable salt, with a suitable base or acid, respectively.

Salts and solvates having non-pharmaceutically acceptable counter-ions or associated solvents are within the scope of the present invention, for example, for use as intermediates in the preparation of other compounds of formula (I) and their pharmaceutically acceptable salts. Thus one embodiment of the invention embraces compounds of formula (I) and salts thereof.

In certain embodiments, compounds according to formula (I) may contain an acidic functional group. Suitable pharmaceutically-acceptable salts include salts of such acidic functional groups. Representative salts include pharmaceutically acceptable metal salts such as sodium, potassium, lithium, calcium, magnesium, aluminum, and zinc salts; carbonates and bicarbonates of a pharmaceutically acceptable metal cation such as sodium, potassium, lithium, calcium, magnesium, aluminum, and zinc; pharmaceutically acceptable organic primary, secondary, and tertiary amines including aliphatic amines, aromatic amines, aliphatic diamines, and hydroxy alkylamines such as methylamine, ethylamine, 2-hydroxyethylamine, diethylamine, TEA, ethylenediamine, ethanolamine, diethanolamine, and cyclohexylamine.

In certain embodiments, compounds according to formula (I) may contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In one embodiment, the pharmaceutically acceptable addition salt is a hydrochloride. In a further embodiment, the pharmaceutically acceptable addition salt is a mandelate such as the (R)-mandelate.

In one embodiment, the invention provides a compound which is:

N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide;

or a pharmaceutically acceptable salt thereof.

In another embodiment, the invention provides a compound which is:

6-(1H-indol-4-yl)-4-(5-{[4-(1-methylethyl)-1-piperazinyl]methyl}-1,3-oxazol-2-yl)-1H-indazole;

or a pharmaceutically acceptable salt thereof.

Compound Preparation

The compounds of the invention may be made by a variety of methods, including standard chemistry. Any previously defined variable will continue to have the previously defined meaning unless otherwise indicated. Illustrative general synthetic methods are set out below and then specific compounds of the invention are prepared in the Examples section.

Process A

Compounds of formula (I), wherein $R^1$, $R^2$, $R^3$ and $R^4$ are as defined above, or salts thereof, may be prepared from compounds of formula (II)

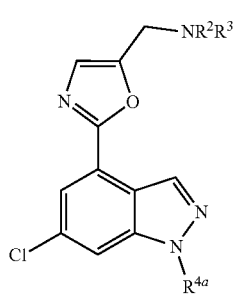

(II)

wherein $R^2$ and $R^3$ are as defined above and $R^{4a}$ is methyl or a suitable protecting group such as benzenesulphonyl, by treatment with a suitable boronic acid or boronate ester such as 4-(4,4,5,5-tetramethyl-1,3,2-dioxaborolan-2-yl)-1H-indole (commercially available), in the presence of a suitable palladium catalyst such as chloro[2'-(dimethylamino)-2-biphenylyl]palladium-(1R,4S)-bicyclo[2.2.1]hept-2-yl[(1S,4R)-bicyclo[2.2.1]hept-2-yl]phosphane, in a suitable solvent such as a mixture of 1,4-dioxane and water in a suitable ratio, for example about 4:1, in the presence of a suitable base such as sodium bicarbonate, and at a suitable temperature such as from about 80° C. to about 150° C., for example about 120° C.

The $R^1$ group introduced via the boronic acid or boronate ester may be protected by a suitable protecting group such as a tert-butyldimethylsilyl group and an additional deprotection step may be required, for example treatment with a suitable fluoride such as tetra-n-butylammonium fluoride, in a suitable solvent such as tetrahydrofuran, and at a suitable temperature such as room temperature, for example about 20° C.

If necessary, for compounds of formula (II) wherein $R^{4a}$ is a suitable protecting group, the protecting group such as benzenesulphonyl may subsequently be removed by treatment with a suitable aqueous inorganic base such as aqueous sodium hydroxide, in a suitable solvent such as isopropanol, and at a suitable temperature such as room temperature, for example about 20° C.

Compounds of formula (II), wherein $R^2$, $R^3$ and $R^{4a}$ are as defined above, may be prepared from compounds of formula (III)

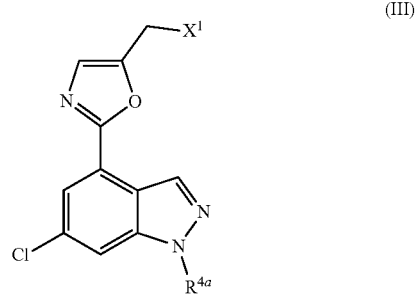

(III)

wherein $R^{4a}$ is as defined above and $X^1$ is a suitable leaving group such as Br, by treatment with an amine of formula $HNR^2R^3$, wherein $R^2$ and $R^3$ are defined as above, in a suitable solvent such as dichloromethane, and at a suitable temperature such as room temperature, for example about 20° C.

Compounds of formula (III), wherein $R^{4a}$ is as defined above and $X^1$ is Br, may be prepared from compounds of formula (IV)

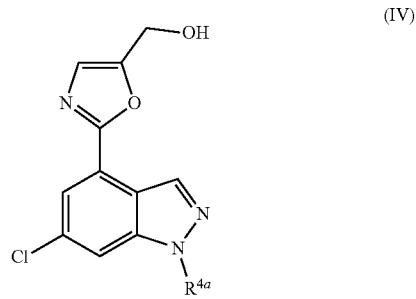

(IV)

wherein $R^{4a}$ is as defined above, by treatment with a suitable brominating agent such as carbon tetrabromide and a suitable phosphine such as triphenylphosphine, in a suitable solvent such as dichloromethane, and at a suitable temperature such as from about 0° C. to about 50° C., for example about 0° C. warming to about 20° C. after addition.

Or, alternatively, compounds of formula (III), wherein $R^{4a}$ is as defined above and $X^1$ is Br, may be prepared from compounds of formula (IV) wherein $R^{4a}$ is as defined above, by treatment with a suitable brominating agent such as triphenylphosphine dibromide, in a suitable solvent such as dichloromethane, and at a suitable temperature such as from about 0° C. to about 50° C., for example about 0° C.

Compounds of formula (IV), wherein $R^{4a}$ is as defined above, may be prepared from compounds of formula (V)

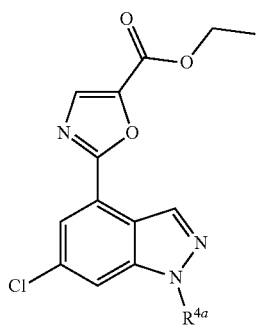

(V)

wherein $R^{4a}$ is as defined above, by treatment with a suitable reducing agent such as diisobutylaluminum hydride, in a suitable solvent such as tetrahydrofuran, and at a suitable temperature such as from about −50° C. to about 0° C., for example about 0° C.

Compounds of formula (V), wherein $R^{4a}$ is as defined above, may be prepared from compounds of formula (VI)

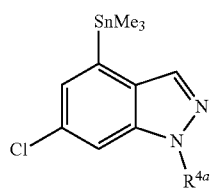

(VI)

wherein $R^{4a}$ is as defined above, by treatment with a suitable halide such as ethyl 2-chloro-1,3-oxazole-5-carboxylate (commercially available), in the presence of a suitable palladium catalyst such as tetrakis(triphenylphosphine)palladium (0), in a suitable solvent such as a N,N-dimethylformamide, in the presence of a suitable iodide such as sodium iodide, and under microwave irradiation at a suitable temperature such as from about 80° C. to about 150° C., for example about 100° C.

Or, alternatively, compounds of formula (V), wherein $R^{4a}$ is as defined above, may be prepared from compounds of formula (VII) as defined below, by treatment with a suitable stannane such as hexamethylditin, in the presence of a suitable palladium catalyst such as tetrakis(triphenylphosphine)palladium (0) and a suitable base such as triethylamine, in a suitable solvent such as toluene, and at a suitable temperature such as from about 100° C. to about 200° C., for example about 120° C., followed by treatment with a suitable halide such as methyl 2-chloro-1,3-oxazole-5-carboxylate (commercially available), in the presence of a suitable iodide such as copper (I) iodide, and a suitable palladium catalyst such as tetrakis(triphenylphosphine)palladium (0), in a suitable solvent such as 1,3-dimethyl-3,4,5,6-tetrahydro-2(1H)-pyrimidinone, and at a suitable temperature such as from about 50° C. to about 150° C., for example about 85° C.

Compounds of formula (VI), wherein $R^{4a}$ is as defined above, may be prepared from compounds of formula (VII)

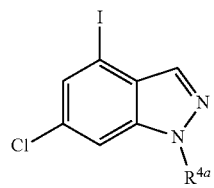

(VII)

wherein $R^{4a}$ is as defined above, by treatment with a suitable stannane such as hexamethylditin, in the presence of a suitable palladium catalyst such as tetrakis(triphenylphosphine)palladium (0), in a suitable solvent such as xylene, in the presence of a suitable base such as triethylamine, and at a suitable temperature such as from about 100° C. to about 200° C., for example about 150° C.

Compounds of formula (VII), wherein $R^{4a}$ is methyl, may be prepared from compounds such as the compound of formula (VIII)

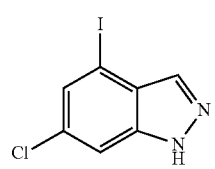

(VIII)

by methylation using a suitable base such as sodium hydride, in a suitable solvent such as tetrahydrofuran, and at a suitable temperature such as about 0° C., followed by addition of an alkylating agent such as iodomethane and stirring at a suitable temperature such as room temperature, for example about 20° C.

The compound of formula (VIII) is commercially available.

Compounds of formula (VII), wherein $R^{4a}$ is a suitable protecting group such as benzenesulphonyl, may be prepared from the compound with formula (VIII) as defined above, by treatment with a suitable base such as sodium hydride in a suitable solvent such as N,N-dimethylformamide, and at a suitable temperature such as from about 0° C. to about 20° C., for example about 0° C., followed by treatment with a suitable sulphonylating agent such as benzensulphonyl chloride, at a suitable temperature such as from about 0° C. to about 50° C., for example about 0° C. warming to about 20° C. after addition.

Or alternatively, compounds of formula (VII), wherein $R^{4a}$ is a suitable protecting group such as benzenesulphonyl, may be prepared from the compound with formula (VIII) as defined above, by treatment with a suitable base, such as sodium hydroxide and a suitable phase transfer catalyst such as tetra-n-butylammonium bisulphate, in a suitable solvent such as tetrahydrofuran and at a suitable temperature such as from about 0° C. to about 20° C., for example about 20° C., followed by treatment with a suitable sulphonylating agent such as benzene sulphonyl chloride, at a suitable temperature such as from about 0° C. to about 50° C., for example about 25° C.

Process B Compounds of formula (I), wherein $R^1$, $R^2$ and $R^3$ are as defined above and $R^4$ is hydrogen, or salts thereof, may be prepared from compounds of formula (IX)

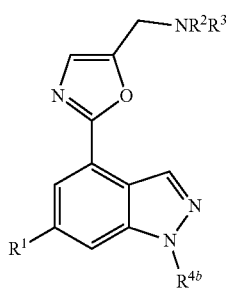

(IX)

wherein $R^1$, $R^2$, $R^3$ are as defined above and $R^{4b}$ is a suitable protecting group such as benzenesulphonyl, by treatment with a suitable aqueous inorganic base such as aqueous sodium hydroxide, in a suitable solvent such as 1,4-dioxane, and at a suitable temperature such as room temperature, for example about 20° C.

Compounds of formula (IX), wherein $R^1$, $R^2$, $R^3$ and $R^{4b}$ are as defined above, may be prepared from compounds of formula (X)

(X)

wherein, $R^1$ and $R^{4b}$ are as defined above and $X^2$ is a suitable leaving group such as Br, by treatment with an amine of formula $HNR^2R^3$, wherein $R^2$ and $R^3$ are as defined above, in a suitable solvent such as dichloromethane, and at a suitable temperature such as room temperature, for example about 20° C.

Compounds of formula (X), wherein $R^1$ and $R^{4b}$ are as defined above and $X^2$ is Br, may be prepared from compounds of formula (XI)

(XI)

wherein $R^1$ and $R^{4b}$ are as defined above, by treatment with a suitable brominating agent such as carbon tetrabromide and a suitable phosphine such as triphenylphosphine, in a suitable solvent such as dichloromethane, and at a suitable temperature such as from about 0° C. to about 50° C., for example about 0° C. warming to room temperature after addition.

Compounds of formula (XI), wherein $R^1$ and $R^{4b}$ are as defined above, may be prepared from compounds of formula (XII)

(XII)

wherein $R^1$ and $R^{4b}$ are as defined above, by treatment with a suitable reducing agent such as diisobutylaluminum hydride, in a suitable solvent such as dichloromethane, and at a suitable temperature such as from about −50° C. to about 0° C., for example about −20° C.

Compounds of formula (XII), wherein $R^1$ and $R^{4b}$ are as defined above, may be prepared from compounds of formula (XIII)

(XIII)

wherein $R^{4b}$ is as defined above, by treatment with a suitable boronic acid or boronate ester such as {1-[(1,1-dimethylethyl)(dimethyl)silyl]-1H-indol-4-yl}boronic acid (commercially available), in the presence of a suitable palladium catalyst such as chloro[2'-(dimethylamino)-2-biphenylyl]palladium-(1R,4S)-bicyclo[2.2.1]hept-2-yl[(1S,4R)-bicyclo[2.2.1]hept-2-yl]phosphane, in a suitable solvent such as a mixture of 1,4-dioxane and water in a suitable ratio, for example about 10:1, in the presence of a suitable base such as potassium phosphate tribasic, and at a suitable temperature such as about 80° C. to about 150° C., for example about 100° C. Alternatively, this process may be carried out under microwave irradiation, and at a suitable temperature such as from about 80° C. to about 150° C., for example about 120° C.

(XIV)

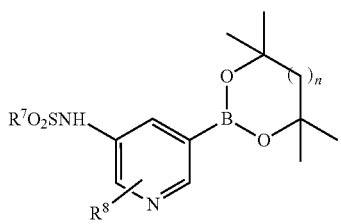

Boronate esters of formula (XIV), wherein $R^7$ is as defined above, $R^8$ is $C_{1-6}$alkyl, —$OR^6$ or halo, wherein $R^6$ is as defined above and n=0 or 1, may be prepared from compounds of formula (XV)

(XV)

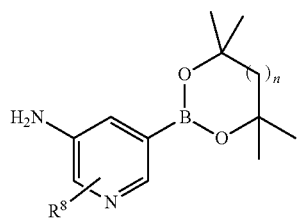

wherein $R^8$ is as defined above and n=0 or 1, by treatment with a suitable sulphonyl chloride of formula $R^7SO_2Cl$ such as methanesulphonyl chloride, in a suitable solvent such as pyridine, and at a suitable temperature such as room temperature, for example about 20° C.

Compounds of formula (XV) wherein $R^8$ is as defined above and n=0 or 1, may be prepared from compounds of formula (XVI)

(XVI)

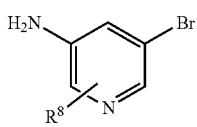

wherein $R^8$ is as defined above, for which a range of analogues are commercially available, by treatment with a suitable borolane such as 4,4,4',4',5,5,5',5'-octamethyl-2,2'-bi-1,3,2-dioxaborolane, in the presence of a suitable palladium catalyst such as dichloro[1,1'-bis(diphenylphosphino)ferrocene]palladium (II) dichloromethane adduct, in the presence of a suitable base such as potassium acetate, in a suitable solvent such as 1,4-dioxane, and at a suitable temperature such as from about 50° C. to about 120° C., for example about 80° C.

Thus, in one embodiment, the invention provides a process for preparing a compound of the invention comprising:

a) reacting a compound of formula (II)

(II)

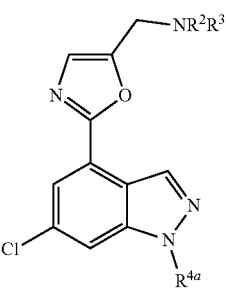

wherein $R^2$ and $R^3$ are as defined above and $R^{4a}$ is methyl or a suitable protecting group, with a suitable boronic acid or boronate ester, followed where necessary by deprotection; or b) for a compound of formula (I) wherein $R^1$, $R^2$ and $R^3$ are as defined above and $R^4$ is hydrogen, reacting a compound of formula (IX)

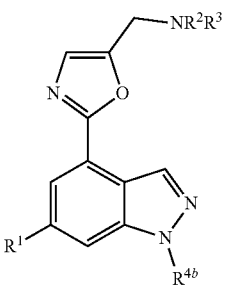

wherein $R^1$, $R^2$, $R^3$ and $R^{4b}$ are as defined above, with a suitable aqeuous inorganic base.

Methods of Use

The compounds of the invention are inhibitors of kinase activity, in particular PI3-kinase activity. Compounds which are PI3-kinase inhibitors may be useful in the treatment of disorders wherein the underlying pathology is (at least in part) attributable to inappropriate PI3-kinase activity, such as asthma and chronic obstructive pulmonary disease (COPD). "Inappropriate PI3-kinase activity" refers to any PI3-kinase activity that deviates from the normal PI3-kinase activity expected in a particular patient. Inappropriate PI3-kinase may take the form of, for instance, an abnormal increase in activity, or an aberration in the timing and or control of PI3-kinase activity. Such inappropriate activity may result then, for example, from overexpression or mutation of the protein kinase leading to inappropriate or uncontrolled activation. Accordingly, in another aspect the invention is directed to methods of treating such disorders.

Such disorders include respiratory diseases including asthma, chronic obstructive pulmonary disease (COPD) and idiopathic pulmonary fibrosis (IPF); viral infections including viral respiratory tract infections and viral exacerbation of respiratory diseases such as asthma and COPD; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain. In one embodiment, such disorders include respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain The methods of treatment of the invention comprise administering a safe and effective amount of a compound of formula (I) or a pharmaceutically acceptable salt thereof to a patient in need thereof. Individual embodiments of the invention include methods of treating any one of the abovementioned disorders by administering a safe and effective amount of a compound of formula (I) or a pharmaceutically acceptable salt thereof to a patient in need thereof.

As used herein, "treat" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

As indicated above, "treatment" of a disorder includes prevention of the disorder. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated;

the medical history of the patient to be treated; the duration of the treatment; the nature of concurrent therapy; the desired therapeutic effect; and like factors, but can nevertheless be routinely determined by the skilled artisan.

As used herein, "patient" refers to a human (including adults and children) or other animal. In one embodiment, "patient" refers to a human.

The compounds of formula (I) or pharmaceutically acceptable salts thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. Inhalation refers to administration into the patient's lungs whether inhaled through the mouth or through the nasal passages. In one embodiment, the compounds of formula (I) or pharmaceutically acceptable salts thereof may be administered orally. In another embodiment, the compounds of formula (I) or pharmaceutically acceptable salts thereof may be administered by inhalation. In a further embodiment, the compounds of formula (I) or pharmaceutically acceptable salts thereof may be administered intranasally.

The compounds of formula (I) or pharmaceutically acceptable salts thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound of formula (I) or a pharmaceutically acceptable salt thereof depend on the pharmacokinetic properties of that compound, such as absorption, distribution, and half-life, which can be determined by the skilled artisan. In addition, suitable dosing regimens, including the duration such regimens are administered, for a compound of formula (I) or a pharmaceutically acceptable salt thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.001 mg to 50 mg per kg of total body weight, for example from 1 mg to 10 mg per kg of total body weight. For example, daily dosages for oral administration may be from 0.5 mg to 2 g per patient, such as 10 mg to 1 g per patient.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of the activity of the compound in vivo;

(b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

In one aspect, the invention thus provides a method of treating a disorder mediated by inappropriate PI3-kinase activity comprising administering a safe and effective amount of a compound of formula (I) or a pharmaceutically acceptable salt thereof to a patient in need thereof. In one embodiment, the invention provides a method of treating a disorder mediated by inappropriate PI3-kinase activity comprising administering a safe and effective amount of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide or a pharmaceutically acceptable salt thereof to a patient in need thereof. In another embodiment, the invention provides a method of treating a disorder mediated by inappropriate PI3-kinase activity comprising administering a safe and effective amount of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (R)-mandelate to a patient in need thereof. In another embodiment, the invention provides a method of treating a disorder mediated by inappropriate PI3-kinase activity comprising administering a safe and effective amount of 6-(1H-indol-4-yl)-4-(5-{[4-(1-methylethyl)-1-piperazinyl]methyl}-1,3-oxazol-2-yl)-1H-indazole or a pharmaceutically acceptable salt thereof to a patient in need thereof. In a further embodiment, the invention provides a method of treating a disorder mediated by inappropriate PI3-kinase activity comprising administering a safe and effective amount of 6-(1H-indol-4-yl)-4-(5-{[4-(1-methylethyl)-1-piperazinyl]methyl}-1,3-oxazol-2-yl)-1H-indazole hydrochloride to a patient in need thereof.

In one embodiment, the disorder mediated by inappropriate PI3-kinase activity is selected from the group consisting of respiratory diseases (including asthma, chronic obstructive pulmonary disease (COPD) and idiopathic pulmonary fibrosis (IPF)); viral infections (including viral respiratory tract infections and viral exacerbation of respiratory diseases such as asthma and COPD); non-viral respiratory infections (including aspergillosis and leishmaniasis); allergic diseases (including allergic rhinitis and atopic dermatitis); autoimmune diseases (including rheumatoid arthritis and multiple sclerosis); inflammatory disorders (including inflammatory bowel disease); cardiovascular diseases (including thrombosis and atherosclerosis); hematologic malignancies; neurodegenerative diseases; pancreatitis; multiorgan failure; kidney diseases; platelet aggregation; cancer; sperm motility; transplantation rejection; graft rejection; lung injuries; and pain (including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain).

In one embodiment, the disorder mediated by inappropriate PI3-kinase activity is a respiratory disease. In another embodiment, the disorder mediated by inappropriate PI3-kinase activity is asthma. In another embodiment, the disorder mediated by inappropriate PI3-kinase activity is chronic obstructive pulmonary disease (COPD). In a further embodiment, the disorder mediated by inappropriate PI3-kinase activity is idiopathic pulmonary fibrosis (IPF).

In one embodiment, the disorder mediated by inappropriate PI3-kinase activity is pain.

In one embodiment, the present invention provides a method of treating a respiratory disease comprising administering a safe and effective amount of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide or a pharmaceutically acceptable salt thereof to a patient in need thereof.

In another embodiment, the present invention provides a method of treating asthma comprising administering a safe and effective amount of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide or a pharmaceutically acceptable salt thereof to a patient in need thereof.

In another embodiment, the present invention provides a method of treating a respiratory disease comprising administering a safe and effective amount of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (R)-mandelate to a patient in need thereof.

In another embodiment, the present invention provides a method of treating asthma comprising administering a safe and effective amount of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (R)-mandelate to a patient in need thereof.

In another embodiment, the present invention provides a method of treating a respiratory disease comprising administering a safe and effective amount of 6-(1H-indol-4-yl)-4-(5-{[4-(1-methylethyl)-1-piperazinyl]methyl}-1,3-oxazol-2-yl)-1H-indazole or a pharmaceutically acceptable salt thereof to a patient in need thereof.

In another embodiment, the present invention provides a method of treating asthma comprising administering a safe and effective amount of 6-(1H-indol-4-yl)-4-(5-{[4-(1-methylethyl)-1-piperazinyl]methyl}-1,3-oxazol-2-yl)-1H-indazole or a pharmaceutically acceptable salt thereof to a patient in need thereof.

In another embodiment, the present invention provides a method of treating a respiratory disease comprising administering a safe and effective amount of 6-(1H-indol-4-yl)-4-(5-{[4-(1-methylethyl)-1-piperazinyl]methyl}-1,3-oxazol-2-yl)-1H-indazole hydrochloride to a patient in need thereof.

In a further embodiment, the present invention provides a method of treating asthma comprising administering a safe and effective amount of 6-(1H-indol-4-yl)-4-(5-{[4-(1-methylethyl)-1-piperazinyl]methyl}-1,3-oxazol-2-yl)-1H-indazole hydrochloride to a patient in need thereof.

In one aspect, the invention provides a compound of formula (I) or a pharmaceutically acceptable salt thereof for use in medical therapy. In one embodiment, the invention provides N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide or a pharmaceutically acceptable salt thereof for use in medical therapy. In another embodiment, the invention provides N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (R)-mandelate for use in medical therapy. In another embodiment, the invention provides 6-(1H-indol-4-yl)-4-(5-{[4-(1-methylethyl)-1-piperazinyl]methyl}-1,3-oxazol-2-yl)-1H-indazole or a pharmaceutically acceptable salt thereof for use in medical therapy. In a further embodiment, the invention provides 6-(1H-indol-4-yl)-4-(5-{[4-(1-methylethyl)-1-piperazinyl]methyl}-1,3-oxazol-2-yl)-1H-indazole hydrochloride for use in medical therapy.

In another aspect, the invention provides a compound of formula (I) or a pharmaceutically acceptable salt thereof for use in the treatment of a disorder mediated by inappropriate PI3-kinase activity. In one embodiment, the invention provides N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide or a pharmaceutically acceptable salt thereof for use in the treatment of a disorder mediated by inappropriate PI3-kinase activity. In another embodiment, the invention provides N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (R)-mandelate or use in the treatment of a disorder mediated by inappropriate PI3-kinase activity. In another embodiment, the invention provides 6-(1H-indol-4-yl)-4-(5-{[4-(1-methylethyl)-1-piperazinyl]methyl}-1,3-oxazol-2-yl)-1H-indazole or a pharmaceutically acceptable salt thereof for use in the treatment of a disorder mediated by inappropriate PI3-kinase activity. In a further embodiment, the invention provides 6-(1H-indol-4-yl)-4-(5-{[4-(1-methylethyl)-1-piperazinyl]methyl}-1,3-oxazol-2-yl)-1H-indazole hydrochloride for use in the treatment of a disorder mediated by inappropriate PI3-kinase activity.

In a further aspect, the invention provides the use of a compound of formula (I) or a pharmaceutically acceptable salt thereof in the manufacture of a medicament for use in the treatment of a disorder mediated by inappropriate PI3-kinase activity. In one embodiment, the invention provides the use of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide or a pharmaceutically acceptable salt thereof in the manufacture of a medicament for use in the treatment of a disorder mediated by inappropriate PI3-kinase activity. In another embodiment, the invention provides the use of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl] methanesulfonamide (R)-mandelate in the manufacture of a medicament for use in the treatment of a disorder mediated by inappropriate PI3-kinase activity. In another embodiment, the invention provides the use of 6-(1H-indol-4-yl)-4-(5-{[4-(1-methylethyl)-1-piperazinyl]methyl}-1,3-oxazol-2-yl)-1H-indazole or a pharmaceutically acceptable salt thereof in the manufacture of a medicament for use in the treatment of a disorder mediated by inappropriate PI3-kinase activity. In a further embodiment, the invention provides the use of 6-(1H-indol-4-yl)-4-(5-{[4-(1-methylethyl)-1-piperazinyl]methyl}-1,3-oxazol-2-yl)-1H-indazole hydrochloride in the manufacture of a medicament for use in the treatment of a disorder mediated by inappropriate PI3-kinase activity.

Compositions

The compounds of formula (I) and pharmaceutically acceptable salts thereof will normally, but not necessarily, be formulated into pharmaceutical compositions prior to administration to a patient.

Accordingly, in one aspect the invention is directed to pharmaceutical compositions comprising a compound of formula (I) or a pharmaceutically acceptable salt thereof and one or more pharmaceutically acceptable excipients.

In one embodiment, the present invention provides a pharmaceutical composition comprising N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide or a pharmaceutically acceptable salt thereof, and one or more pharmaceutically acceptable excipients.

In another embodiment, the present invention provides a pharmaceutical composition comprising N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (R) mandelate, and one or more pharmaceutically acceptable excipients.

In another embodiment, the present invention provides a pharmaceutical composition comprising 6-(1H-indol-4-yl)-4-(5-{[4-(1-methylethyl)-1-piperazinyl]methyl}-1,3-oxazol-2-yl)-1H-indazole or a pharmaceutically acceptable salt thereof, and one or more pharmaceutically acceptable excipients.

In a further embodiment, the present invention provides a pharmaceutical composition comprising 6-(1H-indol-4-yl)-4-(5-{[4-(1-methylethyl)-1-piperazinyl]methyl}-1,3-oxazol-2-yl)-1H-indazole hydrochloride, and one or more pharmaceutically acceptable excipients.

In another aspect the invention is directed to pharmaceutical compositions comprising 0.05 to 1000 mg of a compound of formula (I) or a pharmaceutically acceptable salt thereof and 0.1 to 2 g of one or more pharmaceutically acceptable excipients.

In a further aspect the invention is directed to a pharmaceutical composition for the treatment or prophylaxis of a disorder mediated by inappropriate PI3-kinase activity comprising a compound of formula (I) or a pharmaceutically acceptable salt thereof.

In one embodiment, the present invention is provides a pharmaceutical composition for the treatment or prophylaxis of a disorder mediated by inappropriate PI3-kinase activity comprising N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide or a pharmaceutically acceptable salt thereof.

In one embodiment, the present invention is provides a pharmaceutical composition for the treatment or prophylaxis of a disorder mediated by inappropriate PI3-kinase activity comprising N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (R) mandelate.

In one embodiment, the present invention is provides a pharmaceutical composition for the treatment or prophylaxis of a disorder mediated by inappropriate PI3-kinase activity comprising 6-(1H-indol-4-yl)-4-(5-{[4-(1-methylethyl)-1-piperazinyl]methyl}-1,3-oxazol-2-yl)-1H-indazole or a pharmaceutically acceptable salt thereof.

In a further embodiment, the present invention is provides a pharmaceutical composition for the treatment or prophylaxis of a disorder mediated by inappropriate PI3-kinase activity comprising 6-(1H-indol-4-yl)-4-(5-{[4-(1-methylethyl)-1-piperazinyl]methyl}-1,3-oxazol-2-yl)-1H-indazole hydrochloride.

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.5 mg to 1 g, or from 1 mg to 700 mg, or from 5 mg to 100 mg of a compound of formula (I) or a pharmaceutically acceptable salt thereof.

The pharmaceutical compositions of the invention typically contain one compound of formula (I) or a pharmaceutically acceptable salt thereof.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically-acceptable eg of sufficiently high purity.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company) *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Accordingly, in another aspect the invention is directed to process for the preparation of a pharmaceutical composition comprising a compound of formula (I) or a pharmaceutically acceptable salt thereof and one or more pharmaceutically acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment, the compounds of formula (I) or pharmaceutically acceptable salts thereof will be formulated for oral administration. In another embodiment, the compounds of formula (I) or pharmaceutically acceptable salts thereof will be formulated for inhaled administration. In a further embodiment, the compounds of formula (I) or pharmaceutically acceptable salts thereof will be formulated for intranasal administration.

In one aspect, the invention is directed to a solid oral dosage form such as a tablet or capsule comprising a safe and effective amount of a compound of formula (I) or a pharmaceutically acceptable salt thereof and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of formula (I) or pharmaceutically acceptable salts thereof may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of formula (I) or pharmaceutically acceptable salts thereof may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of formula (I) or a pharmaceutically acceptable salt thereof. Syrups can be prepared by dissolving the compound of formula (I) or a pharmaceutically acceptable salt thereof in a suitably flavored aqueous solution, while elixirs are prepared through the use of a non-toxic alcoholic vehicle. Suspensions can be formulated by dispersing the compound of formula (I) or a pharmaceutically acceptable salt thereof in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In a further embodiment, the invention is directed to a dosage form adapted for administration to a patient by inhalation via a nebulizer.

Dry powder compositions for delivery to the lung by inhalation typically comprise a compound of formula (I) or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 μg-10 mg of the compound of formula (I) or a pharmaceutically acceptable salt thereof.

Aerosols may be formed by suspending or dissolving a compound of formula (I) or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

There is thus provided as a further aspect of the invention a pharmaceutical aerosol formulation comprising a compound of formula (I) or a pharmaceutically acceptable salt thereof and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Capsules and cartridges for use in an inhaler or insufflator, of for example gelatine, may be formulated containing a powder mix for inhalation of a compound of formula (I) or a pharmaceutically acceptable salt thereof and a suitable powder base such as lactose or starch. Each capsule or cartridge may generally contain from 20 μg to 10 mg of the compound of formula (I) or pharmaceutically acceptable salt thereof. Alternatively, the compound of formula (I) or pharmaceutically acceptable salt thereof may be presented without excipients such as lactose.

The proportion of the active compound of formula (I) or pharmaceutically acceptable salt thereof in the local compositions according to the invention depends on the precise type of formulation to be prepared but will generally be within the range of from 0.001 to 10% by weight. Generally, for most types of preparations, the proportion used will be within the range of from 0.005 to 1%, for example from 0.01 to 0.5%. However, in powders for inhalation or insufflation the proportion used will normally be within the range of from 0.1 to 5%.

Aerosol formulations are preferably arranged so that each metered dose or "puff" of aerosol contains from 20 μg to 10 mg, preferably from 20 μg to 2000 μg, more preferably from about 20 μg to 5004 of a compound of formula (I). Administration may be once daily or several times daily, for example 2, 3, 4 or 8 times, giving for example 1, 2 or 3 doses each time. The overall daily dose with an aerosol will be within the range from 100 μg to 10 mg, preferably from 2004 to 20004. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and a compound of formula (I) or a pharmaceutically acceptable salt thereof in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

The term "metered dose inhaler" or MDI means a unit comprising a can, a secured cap covering the can and a formulation metering valve situated in the cap. MDI system includes a suitable channeling device. Suitable channeling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO96/32099). Preferably the canister is fitted with a cap assembly, wherein a drug-metering valve is situated in the cap, and said cap is crimped in place.

In one embodiment of the invention the metallic internal surface of the can is coated with a fluoropolymer, more preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example bulk manufacturing method for preparing solution aerosol formulations a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Suspensions and solutions comprising a compound of formula (I) or a pharmaceutically acceptable salt thereof may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of formula (I) or pharmaceutically acceptable salt thereof may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of formula (I) or pharmaceutically acceptable salt thereof. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

In a further aspect, the invention is directed to a dosage form adapted for intranasal administration.

Formulations for administration to the nose may include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

The compounds of formula (I) or pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO05/044354.

Pharmaceutical compositions adapted for intranasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the compound of formula (I) or a pharmaceutically acceptable salt thereof.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as *arachis* oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound of formula (I) or a pharmaceutically acceptable salt thereof may be employed with either a paraffinic or a water-miscible ointment base. Alternatively, the compound of formula (I) or pharmaceutically acceptable salt thereof may be formulated in a cream with an oil-in-water cream base or a water-in-oil base.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The compound and pharmaceutical formulations according to the invention may be used in combination with or include one or more other therapeutic agents, for example selected from anti-inflammatory agents, anticholinergic agents (particularly an $M_1/M_2/M_3$ receptor antagonist), $β_2$-adrenoreceptor agonists, antiinfective agents, such as antibiotics or antivirals, or antihistamines. The invention thus provides, in a further aspect, a combination comprising a compound of formula (I) or a pharmaceutically acceptable salt thereof together with one or more other therapeutically active agents, for example selected from an anti-inflammatory agent, such as a corticosteroid or an NSAID, an anticholinergic agent, a β₂-adrenoreceptor agonist, an anti-infective agent, such as an antibiotic or an antiviral, or an antihistamine. One embodiment of the invention encompasses combinations comprising a compound of formula (I) or a pharmaceutically acceptable salt thereof together with a β₂-adrenoreceptor agonist, and/or an anticholinergic, and/or a PDE-4 inhibitor, and/or an antihistamine.

In one embodiment, the invention encompasses a method of treating a disorder mediated by inappropriate PI3-kinase activity comprising administering a safe and effective amount of a combination comprising a compound of formula (I) or a pharmaceutically acceptable salt thereof together with one or more therapeutically active agents.

Certain compounds of the invention may show selectivity for PI3Kδ over other PI3-kinases. The invention thus provides, in a further aspect, a combination comprising a compound of formula (I) or a pharmaceutically acceptable salt thereof which is selective for PI3Kδ together with a compound or pharmaceutically acceptable salt thereof which is selective for another PI3-kinase, for example PI3Kγ.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising a compound of formula (I) or a pharmaceutically acceptable salt thereof together with a β₂-adrenoreceptor agonist.

Examples of β₂-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single duastereomer such as the R,R-diastereomer), salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment, long-acting β₂-adrenoreceptor agonists, for example, compounds which provide effective bronchodilation for about 12 hrs or longer, are preferred.

Other β₂-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Examples of β₂-adrenoreceptor agonists include:
3-(4-{[6-({(2R)-2-hydroxy-2-[4-hydroxy-3-(hydroxymethyl)phenyl]ethyl}amino) hexyl] oxy} butyl) benzenesulfonamide;
3-(3-{[7-({(2R)-2-hydroxy-2-[4-hydroxy-3-hydroxymethyl) phenyl] ethyl}-amino) heptyl] oxy} propyl) benzenesulfonamide;
4-{(1R)-2-[(6-{2-[(2,6-dichlorobenzyl) oxy] ethoxy} hexyl) amino]-1-hydroxyethyl}-2-(hydroxymethyl) phenol;
4-{(1R)-2-[(6-{4-[3-(cyclopentylsulfonyhphenyl] butoxy}hexyl) amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl] phenyl]formamide;
N-2{2-[4-(3-phenyl-4-methoxyphenyl)aminophenyl] ethyl}-2-hydroxy-2-(8-hydroxy-2(1H)-quinolinon-5-yl) ethylamine; and
5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The β₂-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Suitable anti-inflammatory agents include corticosteroids. Suitable corticosteroids which may be used in combination with the compounds of formula (I) or pharmaceutically acceptable salts thereof are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-1β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,2α-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-1β-hydroxy-16α-methyl-3-oxo-androsta-1,4-diene-17β-carbothioic acid S-fluoromethyl ester, 6α,9α-difluoro-1β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methylcyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Examples of corticosteroids may include those described in WO2002/088167, WO2002/100879, WO2002/12265, WO2002/12266, WO2005/005451, WO2005/005452, WO2006/072599 and WO2006/072600.

Non-steroidal compounds having glucocorticoid agonism that may possess selectivity for transrepression over transactivation and that may be useful in combination therapy include those covered in the following patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651 and WO03/08277. Further non-steroidal compounds are covered in: WO2006/000401, WO2006/000398 and WO2006/015870.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO93/13055, WO98/30537, WO02/50021, WO95/34534 and WO99/62875. Examples of CCR3 inhibitors include those disclosed in WO02/26722.

In one embodiment, the invention provides the use of the compounds of formula (I) in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 September. 1996; this patent and the compounds it discloses are incorporated herein in full by reference.

Other compounds include AWD-12-281 from Elbion (Hofgen, N. et al. 15th EFMC Int Symp Med Chem (September 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-etl)oxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from *Vernalis*; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd) (e.g. Example 399 or 544 disclosed therein). Further compounds are also disclosed in WO2005/058892, WO2005/090348, WO2005/090353, and WO2005/090354, all in the name of Glaxo Group Limited.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Additional compounds are disclosed in WO 2005/037280, WO 2005/046586 and WO 2005/104745, incorporated herein by reference. The present combinations include, but are not limited to:
(3-endo)-3-(2,2-di-2-thienylethenyl)-8,8-dimethyl-8-azoniabicyclo[3.2.1]octane iodide;
(3-endo)-3-(2-cyano-2,2-diphenylethyl)-8,8-dimethyl-8-azoniabicyclo[3.2.1]octane bromide;
4-[hydroxy(diphenyl)methyl]-1-{2-[(phenylmethyl)oxy]ethyl}-1-azoniabicyclo[2.2.2]octane bromide; and
(1R,5S)-3-(2-cyano-2,2-diphenylethyl)-8-methyl-8-{2-[(phenylmethyl)oxy]ethyl}-8-azoniabicyclo[3.2.1]octane bromide.

Other anticholinergic agents include compounds which are disclosed in U.S. patent application 60/487,981 including, for example:
(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methylbenzenesulfonate;
(3-endo)-8,8-dimethyl-3-[2-phenyl-2-(2-thienylethenyl]-8-azoniabicyclo[3.2.1]octane bromide; and/or
(3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511,009 including, for example:
(endo)-3-(2-methoxy-2,2-di-thiophen-2-yl-ethyl)-8,8-dimethyl-8-azonia-bicyclo[3.2.1]octane iodide;
3-((endo)-8-methyl-8-aza-bicyclo[3.2.1]oct-3-yl)-2,2-diphenyl-propionitrile; (endo)-8-methyl-3-(2,2,2-triphenyl-ethyl)-8-aza-bicyclo[3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
3-((endo)-8-methyl-8-aza-bicyclo[3.2.1]oct-3-yl)-2,2-diphenyl-propan-1-01;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or
(endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

In one embodiment the invention provides a combination comprising a compound of formula (I) or a pharmaceutically acceptable salt thereof together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of formula (I) or a pharmaceutically acceptable salt thereof together with an H3 antagonist (and/or inverse agonist). Examples of H3 antagonists include, for example, those compounds disclosed in WO2004/035556 and in WO2006/045416. Other histamine receptor antagonists which may be used in combination with the compounds of the present invention include antagonists (and/or inverse agonists) of the H4 receptor, for example, the compounds disclosed in Jablonowski et al., *J. Med. Chem.* 46:3957-3960 (2003).

The invention thus provides, in a further aspect, a combination comprising a compound of formula (I) or a pharmaceutically acceptable salt thereof together with a PDE4 inhibitor.

The invention thus provides, in a further aspect, a combination comprising a compound of formula (I) or a pharmaceutically acceptable salt thereof together with a $\beta_2$-adrenoreceptor agonist.

The invention thus provides, in a further aspect, a combination comprising a compound of formula (I) or a pharmaceutically acceptable salt thereof together with a corticosteroid.

The invention thus provides, in a further aspect, a combination comprising a compound of formula (I) or a pharmaceutically acceptable salt thereof together with a non-steroidal GR agonist.

The invention thus provides, in a further aspect, a combination comprising a compound of formula (I) or a pharmaceutically acceptable salt thereof together with an anticholinergic.

The invention thus provides, in a further aspect, a combination comprising a compound of formula (I) or a pharmaceutically acceptable salt thereof together with an antihistamine.

The invention thus provides, in a further aspect, a combination comprising a compound of formula (I) or a pharmaceutically acceptable salt thereof together with a PDE4 inhibitor and a $\beta_2$-adrenoreceptor agonist.

The invention thus provides, in a further aspect, a combination comprising a compound of formula (I) or a pharmaceutically acceptable salt thereof together with an anticholinergic and a PDE-4 inhibitor.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of formula (I) or a pharmaceutically acceptable salt thereof together with another therapeutically active agent.

The invention thus provides, in a further aspect, a pharmaceutical composition comprising a combination of a compound of formula (I) or a pharmaceutically acceptable salt thereof together with a PDE4 inhibitor.

The invention thus provides, in a further aspect, a pharmaceutical composition comprising a combination of a compound of formula (I) or a pharmaceutically acceptable salt thereof together with a $\beta_2$-adrenoreceptor agonist.

The invention thus provides, in a further aspect, a pharmaceutical composition comprising a combination of a compound of formula (I) or a pharmaceutically acceptable salt thereof together with a corticosteroid.

The invention thus provides, in a further aspect, a pharmaceutical composition comprising a combination of a compound of formula (I) or a pharmaceutically acceptable salt thereof together with a non-steroidal GR agonist.

The invention thus provides, in a further aspect, a pharmaceutical composition comprising a combination of a compound of formula (I) or a pharmaceutically acceptable salt thereof together with an anticholinergic.

The invention thus provides, in a further aspect, a pharmaceutical composition comprising a combination of a compound of formula (I) or a pharmaceutically acceptable salt thereof together with an antihistamine.

The invention thus provides, in a further aspect, a pharmaceutical composition comprising a combination of a compound of formula (I) or a pharmaceutically acceptable salt thereof together with a PDE4 inhibitor and a $\beta_2$-adrenoreceptor agonist.

The invention thus provides, in a further aspect, a pharmaceutical composition comprising a combination of a compound of formula (I) or a pharmaceutically acceptable salt thereof together with an anticholinergic and a PDE4 inhibitor.

The invention will now be illustrated by way of the following non-limiting examples.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

When the name of a commercial supplier is given after the name of a compound or a reagent, for instance "compound X (Aldrich)" or "compound)(Aldrich", this means that compound X is obtainable from a commercial supplier, such as the commercial supplier named. If not referenced herein the compound or reagent can be purchased from a standard supplier such as Sigma Aldrich, Lancaster, Fluorochem, TCI etc.

The names of the Examples have been obtained using a compound naming programme which matches structure to name (e.g. ACD/Name Batch v 9.0).

General Experimental Details

Liquid Chromatography Mass Spectroscopy (LCMS) Methods LCMS analysis has been carried out using one of the methods listed below.

Method A:

LCMS instrumentation consists of the following:
Column: Acquity UPLC BEH $C_{18}$ 1.7 μm 2.1 mm×50 mm. Column oven set to 40 degrees centigrade Solvent A: Water 0.1% Formic Acid+10 mM Ammonium Acetate
Solvent B: MeCN: Water 95:5+0.05% Formic Acid

| Time | Flow ml/min | % A | % B |
|---|---|---|---|
| 0 | 1 | 97 | 3 |
| 0.1 | 1 | 97 | 3 |
| 1.4 | 1 | 0 | 100 |
| 1.9 | 1 | 0 | 100 |
| 2 | 1 | 97 | 3 |

Method B:

The HPLC analysis was conducted on a Sunfire C18 column (30 mm×4.6 mm i.d. 3.5 μm packing diameter) at 30 degrees centigrade.

Solvent A=0.1% v/v solution of Formic Acid in Water.
Solvent B=0.1% v/v solution of Formic Acid in Acetonitrile.

The gradient employed was:

| Time (min) | Flow Rate (ml/min) | % A | % B |
|---|---|---|---|
| 0 | 3 | 97 | 3 |
| 0.1 | 3 | 97 | 3 |
| 4.2 | 3 | 0 | 100 |
| 4.8 | 3 | 0 | 100 |
| 4.9 | 3 | 97 | 3 |
| 5.0 | 3 | 97 | 3 |

The UV detection was an averaged signal from wavelength of 210 nm to 350 nm and mass spectra were recorded on a mass spectrometer using alternate-scan positive and negative mode electrospray ionization.

Method C:

The HPLC analysis was conducted on a Phenomenex Luma C18(2) (50 mm×2 mm i.d. 3 μm packing diameter, or validated equivalent) at 40 degrees centigrade.

Solvent A=0.05% v/v solution of TFA in Water.
Solvent B=0.05% v/v solution of TFA in Acetonitrile.

The gradient employed was:

| Time (min) | Flow Rate (ml/min) | % A | % B |
|---|---|---|---|
| 0 | 1 | 100 | 0 |
| 8 | 1 | 5 | 95 |
| 8.01 | 1 | 100 | 0 |

The UV detection wavelength was analyte dependent and mass spectra were recorded on a mass spectrometer using positive ion electrospray.

Method D:

The HPLC analysis was conducted on a Phenomenex Luma C18(2) (50 mm×2 mm i.d. 3 μm packing diameter, or validated equivalent) at 60 degrees centigrade.

Solvent A=0.05% v/v solution of TFA in Water.
Solvent B=0.05% v/v solution of TFA in Acetonitrile.

The gradient employed was:

| Time (min) | Flow Rate (ml/min) | % A | % B |
|---|---|---|---|
| 0 | 1.5 | 100 | 0 |
| 2.5 | 1.5 | 5 | 95 |
| 2.7 | 1.5 | 5 | 95 |
| 2.9 | 1.5 | 100 | 0 |

The UV detection wavelength was analyte dependent and mass spectra were recorded on a mass spectrometer using positive ion electrospray.

Mass Directed Automated Preparative HPLC Methods

The methods for the mass-directed automated preparative HPLC used for the purification of compounds are described below:

Method A—High pH

Column Details: Waters_XBRIDGE Prep C18 column 5 um OBD (30×150 mm)

The solvents employed were:

A=10 mM Ammonium Bicarbonate in water adjusted to pH 10 with aq. Ammonia solution B=Acetontrile+0.1% aq. Ammonia Collection was triggered by uv, ms or a combination of the two. The UV detection was an averaged signal from wavelength of 210 nm to 350 nm. Mass spectra were recorded on a mass spectrometer using an alternate-scan positive and negative mode electrospray ionization.

Method B—Low pH

Column Details: SUNFIRE C18 column (30×150 mm id 5 uM packing diameter)

The solvents employed were:

A=0.1% v/v solution of Formic Acid in Water.

B=0.1% v/v solution of Formic Acid in Acetontrile.

Collection was triggered by uv, ms or a combination of the two. The UV detection was an averaged signal from wavelength of 210 nm to 350 nm. Mass spectra were recorded on a mass spectrometer using an alternate-scan positive and negative mode electrospray ionization.

Method C

Column Details: XBRIDGE Shield RPI8 column (100×19 mm, 5 uM packing diameter

The solvents employed were:

A=10 mM Ammonium Bicarbonate in water adjusted to pH 10 with aq. Ammonia solution B=Methanol Collection was triggered by uv, ms or a combination of the two. The UV detection was an averaged signal from wavelength of 210 nm to 350 nm. Mass spectra were recorded on a mass spectrometer using an alternate-scan positive and negative mode electrospray ionization.

Intermediates and Examples

Intermediate 1

6-Chloro-4-iodo-1-(phenylsulfonyl)-1H-indazole

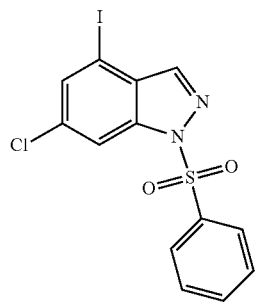 [SMILES: O=S(=O)(c1ccccc1)n1ncc2c(I)cc(Cl)cc21]

Method A

6-Chloro-4-iodo-1H-indazole (30 g, 108 mmol, available from Sinova) was dissolved in N,N-dimethylformamide (300 ml) and cooled in an ice water bath under nitrogen. Sodium hydride (5.17 g, 129 mmol) was added portionwise, maintaining the temperature below 10° C. After full addition the reaction mixture was stirred for 20 mins then benzenesulfonyl chloride (16.5 ml, 129 mmol) was added dropwise over 15 mins. The reaction was left to warm to RT overnight then poured onto ice water (2 L). The precipitated product was collected by filtration, washed with water (ca. 400 ml) and dried in a vacuum oven overnight to give the title compound (43.3 g).

LCMS (Method A): Rt 1.38 mins, MH$^+$ 419.

Method B

To a stirred solution of 6-chloro-4-iodo-1H-indazole (633.6 g) in THF (5.7 L) was added sodium hydroxide (227.4 g) followed by tetra-n-butylammonium bisulphate (38.0 g) at 20±3° C., under a nitrogen atmosphere. The mixture was stirred at 20±3° C. for 1 h 3 min, then benzenesulphonyl chloride (319 ml) was added at such a rate as to maintain the internal temperature at <25° C. Residual benzenesulphonyl chloride was rinsed into the vessel with THF (630 mL), then the mixture stirred for 1 h 10 min. The mixture was cooled to <5° C. and water (12.7 L) added at such a rate as to maintain internal temperature below 5±3° C., then the mixture stirred at 0-5° C. for 1 h 20 min. The solids were collected by vacuum filtration, washed with water (2×1.9 L), sucked dry then further dried under vacuum with a nitrogen bleed at 40° C.±3° C. overnight to give the title compound (780.8 g).

LCMS (Method C): Rt 6.28 min, MH$^+$ 419.

Intermediate 2

6-Chloro-1-(phenylsulfonyl)-4-(trimethylstannanyl)-1H-indazole

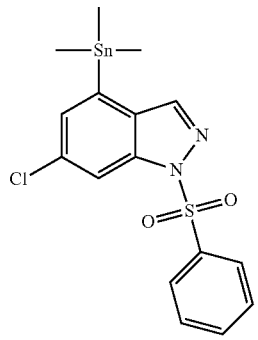 [SMILES: [CH3][Sn]([CH3])([CH3])[c]1cc(Cl)cc2c1cnn2S(=O)(=O)c1ccccc1]

6-Chloro-4-iodo-1-(phenylsulfonyl)-1H-indazole (30 g, 71.7 mmol), tetrakis(triphenylphosphine)palladium(0) (8.1 g, 7.01 mmol), xylene (200 ml), triethylamine (19.98 ml, 143 mmol) and hexamethylditin (21.8 ml, 105 mmol) were heated at 150° C. for 2 h. The reaction mixture was filtered hot through Celite, washing with further xylene and the solvent was evaporated in vacuo. The residue was triturated with cyclohexane and the precipitate collected by filtration and dried in a vacuum oven to give the title compound (14.4 g).

LCMS (Method A): Rt 1.51 mins, MH$^+$ 457.

Intermediate 3a

Ethyl 2-[6-chloro-1-(phenylsulfonyl)-1H-indazol-4-yl]-1,3-oxazole-5-carboxylate

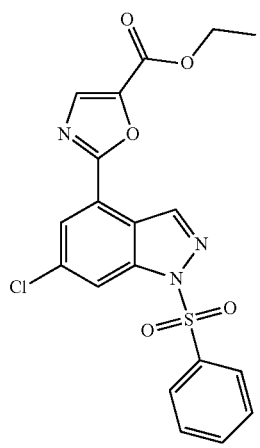 [SMILES: CCOC(=O)c1cnc(-c2cc(Cl)cc3c2cnn3S(=O)(=O)c2ccccc2)o1]

In 4 batches, tetrakis(triphenylphosphine)palladium(0) (3.37 g, 2.92 mmol), ethyl 2-chloro-1,3-oxazole-5-carboxylate (6.65 g, 37.9 mmol, available from Apollo Scientific) and copper(I) iodide (1.11 g, 5.83 mmol) were added to a solution of 6-chloro-1-(phenylsulfonyl)-4-(trimethylstannanyl)-1H-indazole (13.28 g, 29.2 mmol) in N,N-dimethylformamide (52 ml). In 3 of the batches, tetrakis(triphenylphosphine)palladium(0) (1.03 g, 0.89 mmol), ethyl 2-chloro-1,3-oxazole-5-carboxylate (2.03 g, 11.59 mmol) and copper(I) iodide (0.34 g, 1.78 mmol) were added to a solution of 6-chloro-1-(phenylsulfonyl)-4-(trimethylstannanyl)-1H-indazole (4.06 g, 8.91 mmol) in N,N-dimethylformamide (16 ml). In the fourth batch, tetrakis(triphenylphosphine)palladium(0) (0.28 g, 0.24 mmol), ethyl 2-chloro-1,3-oxazole-5-carboxylate (0.55 g, 3.14 mmol) and copper(I) iodide (0.09 g, 0.48 mmol) were added to a solution of 6-chloro-1-(phenylsulfonyl)-4-(trimethylstannanyl)-1H-indazole (1.10 g, 2.42 mmol) in N,N-dimethylformamide (4 ml). Each batch was heated and stirred at 100° C. under microwave irradiation for 30 min. The mixtures were allowed to cool to RT and the combined precipitated product suspended in diethyl ether and collected by filtration, washing with further diethyl ether then drying in a vacuum oven for 72 h. Approximately 5.2 g of the resultant solid was dissolved in dichloromethane and passed through Celite, eluting with further dichloromethane. The solvent was evaporated in vacuo to give the title compound as a pale orange solid (4.95 g).

LCMS (Method A): Rt 1.38 mins, MH$^+$ 432.

Intermediate 3b

Methyl 2-[6-chloro-1-(phenylsulfonyl)-1H-indazol-4-yl]-1,3-oxazole-5-carboxylate

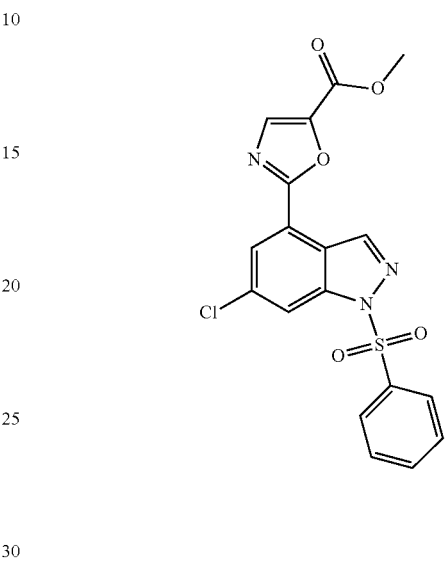

To a stirred solution of 6-chloro-4-iodo-1-(phenylsulphonyl)-1H-indazole (549.8 g) in toluene (1.43 L) was added triethylamine (380 ml) at 20±3° C. under an atmosphere of nitrogen. Hexamethylditin (385 ml) in toluene (825 ml) was added, followed by toluene (275 ml) then tetrakis(triphenylphosphine) palladium (0) (154.7 g). The reaction mixture was heated to 120° C. and stirred at this temperature for 3 h. The mixture was allowed to cool to 20±3° C., filtered, then washed with toluene (4.95 L). The filtrate was transferred to a clean vessel through a 5 µm Dominick hunter in-line filter, rinsing with further toluene (550 ml). The batch was then washed with 50% aqueous KF solution (5.5 L), the aqueous slurry filtered and the filtrate recombined with the organic phase. The aqueous was separated and the organics washed successively with 50% aqueous KF (5.5 L), followed by water (5.5 L). The organic layer was diluted with DMPU (2.75 L) then concentrated by vacuum distillation to ca. 5.4 vols. To the resultant solution was added copper (I) iodide (25.5 g) followed by methyl 2-chloro-1,3-oxazole-5-carboxylate (279 g, available from Apollo Scientific) at 20±3° C. The solution was degassed via vacuum and nitrogen purges (×3). Tetrakis(triphenylphosphine) palladium (0) (78 g) was added, the mixture degassed (×3) and then heated to 85-90° C. for 10 h. The mixture was diluted with DMSO (13.75 L) and cooled to 20±3° C., then water (2.75 L) added in ca. 1 vol portions over ca. 15 mins until crystallisation was initiated. The resultant suspension was aged at 20° C.±3° C. for 1.5 h. The solids were collected by vacuum filtration, washed with water (2×2.75 L), sucked dry and then further dried in vacuo with a nitrogen bleed at 45° C.±5° C. overnight to give the title compound (341.1 g).

LCMS (Method C): Rt 6.08 mins, MH$^+$ 418

Intermediate 4

{2-[6-Chloro-1-(phenylsulfonyl)-1H-indazol-4-yl]-1,3-oxazol-5-yl}methanol

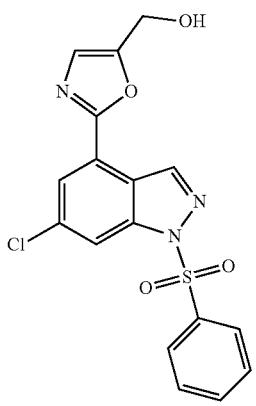 [SMILES: O=S(=O)(c1ccccc1)n1ncc2c(-c3ncc(CO)o3)cc(Cl)cc21]

Method A

A solution of ethyl 2-[6-chloro-1-(phenylsulfonyl)-1H-indazol-4-yl]-1,3-oxazole-5-carbon/late (5.11 g, 11.8 mmol) in dichloromethane (80 ml) was cooled to −25° C. in an oven dried round bottomed flask. Diisobutylaluminium hydride (25 ml, 37.5 mmol, 1.5M solution in toluene) was added dropwise and the reaction stirred at −20° C. for 3 h. A 10% aqueous solution of potassium sodium tartrate (80 ml) was added and the reaction mixture stirred for 5 min. The precipitated solid was filtered off and partitioned between ethyl acetate (500 ml) and water (500 ml). The layers were separated and the aqueous washed with further ethyl acetate (3×150 ml). The combined organics were dried and evaporated in vacuo to give the title compound as a yellow solid (1.1 g).

LCMS (Method A): Rt 1.09 mins, MH+ 390.

The remaining filtrate was largely concentrated in vacuo and the residue partitioned between ethyl acetate (500 ml) and water (500 ml). The layers were separated and the aqueous extracted with further ethyl acetate (3×150 ml). The combined organics were washed with water (2×150 ml), dried over anhydrous sodium sulfate and evaporated to give the title compound as a yellow solid (1.9 g).

LCMS (Method A): Rt 1.09 mins, MH+ 390.

Method B

To a solution of ethyl 2-[6-chloro-1-(phenylsulfonyl)-1H-indazol-4-yl]-1,3-oxazole-5-carbon/late (1.15 g) in THF (17.25 ml), stirred under nitrogen in an ice bath was added a solution of diisobutylaluminium hydride (5.08 ml, 5.64 mmol) in toluene. The reaction mixture was stirred at 0° C. for 2 h. Sodium sulphate decahydrate (2.5 g) was added, the mixture stirred at RT for 1 h, then filtered, washed with THF (2×5 vols) and concentrated under reduced pressure to give the title compound (0.98 g).

LCMS (Method D): Rt 2.20 mins, MH+ 390.

Intermediate 5

4-[5-(Bromomethyl)-1,3-oxazol-2-yl]-6-chloro-1-(phenylsulfonyl)-1H-indazole

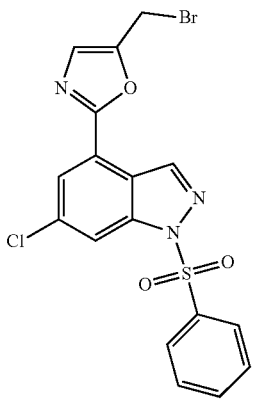 [SMILES: O=S(=O)(c1ccccc1)n1ncc2c(-c3ncc(CBr)o3)cc(Cl)cc21]

Method A

{2-[6-Chloro-1-(phenylsulfonyl)-1H-indazol-4-yl]-1,3-oxazol-5-yl}methanol (1.626 g, 4.17 mmol) was dissolved in anhydrous dichloromethane (20 ml) and carbon tetrabromide (2.77 g, 8.34 mmol) added. The reaction mixture was cooled to 0° C. and a solution of triphenylphosphine (2.188 g, 8.34 mmol) in dichloromethane (20 ml) added dropwise. After allowing to warm to RT and stirring for a further 3 h, the solvent was partially removed in vacuo and the solution purified directly by silica gel chromatography, eluting with 0-100% ethyl acetate in dichloromethane. The appropriate fractions were combined to give the title compound as a cream solid (1.16 g).

LCMS (Method B): Rt 3.70 mins, MH+ 454.

Method B

Triphenylphosphine dibromide (20.60 g, 48.8 mmol) was added to a suspension of {2-[6-chloro-1-(phenylsulfonyl)-1H-indazol-4-yl]-1,3-oxazol-5-yl}methanol (9.06 g, 23.2 mmol) in dichloromethane (181 ml) at 0° C. The reaction mixture was stirred at 0° C. until completion. Water (91 ml) and saturated sodium bicarbonate solution (91 ml) were added and the mixture stirred, then separated. The aqueous layer was extracted with further dichloromethane (45 ml) and the organics combined and washed with water (91 ml). The layers were separated and the organic concentrated to dryness then redissolved in methanol (136 ml). After stirring for 30 mins the resultant white suspension was filtered and the solid dried under vacuum to give the title compound as an off-white solid (9.58 g). LCMS (Method D): Rt 2.57 min, MH+ 452/454.

Intermediate 6a

6-Chloro-4-(5-{[(2R,6S)-2,6-dimethyl-4-morpholinyl]methyl}-1,3-oxazol-2-yl)-1-(phenylsulfonyl)-1H-indazole

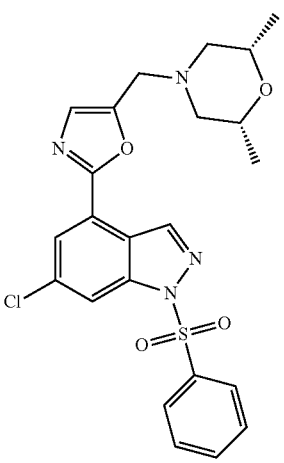 [SMILES: C[C@@H]1CN(Cc2cnc(-c3cc(Cl)cc4c3cnn4S(=O)(=O)c3ccccc3)o2)C[C@H](C)O1]

4-[5-(Bromomethyl)-1,3-oxazol-2-yl]-6-chloro-1-(phenylsulfonyl)-1H-indazole (0.580 g, 1.28 mmol) was dissolved in dichloromethane (5 ml) and (2R,6S)-2,6-dimethylmorpholine (0.317 ml, 2.56 mmol) added. The reaction mixture was stirred at RT for 3 h then the solvent removed under a stream of nitrogen. The resultant yellow solid was dissolved in dichloromethane (5 ml) and washed with water (2×2.5 ml). The layers were separated (hydrophobic frit) and the organic evaporated in vacuo to give the title compound as a pale yellow solid (0.60 g).

LCMS (Method A): Rt 0.86 mins, MH$^+$ 487.

$^1$H NMR (400 MHz, Chloroform-d) δ (ppm) 8.93 (d, J=1.0 Hz, 1H), 8.33 (dd, J=1.0, 1.5 Hz, 1H), 8.04-8.00 (m, 2H), 7.98 (d, J=1.5 Hz, 1H), 7.62 (tt, J=1.5, 7.5 Hz, 1H), 7.51 (t, J=7.5 Hz, 2H), 7.15 (s, 1H), 3.67 (s, 2H), 3.75-3.66 (m, 2H), 2.79-2.72 (m, 2H), 1.86 (dd, J=10.5, 11.0 Hz, 2H), 1.16 (d, J=6.5 Hz, 6H).

Similarly prepared using the appropriate amine was:

Intermediate 7

2-(Methyloxy)-5-(4,4,5,5-tetramethyl-1,3,2-dioxaborolan-2-yl)-3-pyridinamine

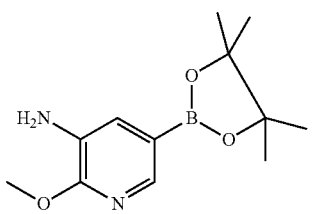

To 5-bromo-2-(methyloxy)-3-pyridinamine (18.93 g, 93 mmol, available from Asymchem International) in a 1 L round-bottom flask was added nitrogen-purged 1,4-dioxane (500 ml) followed by 4,4,4',4',5,5,5',5'-octamethyl-2,2'-bi-1,3,2-dioxaborolane (47.4 g, 186 mmol), potassium acetate (27.5 g, 280 mmol) and dichloro{1,1'-bis(diphenylphosphino)ferrocene]palladium (II) dichloromethane adduct (7.61 g, 9.32 mmol). The mixture was then stirred at 80° C. under nitrogen for 2 h. The reaction mixture was allowed to cool then partitioned between ethyl acetate and water and filtered through a Celite pad. The aqueous layer was extracted further with ethyl acetate (2×) and the combined organics washed with water, brine and dried over magnesium sulphate overnight. The mixture was filtered and the filtrate concentrated in vacuo to give a dark brown solid. The residue was purified by silica gel chromatography, eluting in 0-50% ethyl acetate/dichloromethane. The appropriate fractions were combined and evaporated to dryness and the residue triturated with cyclohexane. The resultant solid was filtered off and dried in vacuo to give the title compound as a light pink solid (11.1 g).

LCMS (Method A) Rt 0.91 mins, MH$^+$ 251.

| Intermediate Number | Name | Structure | Amine | LC/MS R$_t$ min | LC/MS MH$^+$ |
|---|---|---|---|---|---|
| 6b | 6-chloro-4-(5-{[4-(1-methylethyl)-1-piperazinyl]methyl}-1,3-oxazol-2-yl)-1-(phenylsulfonyl)-1H-indazole | 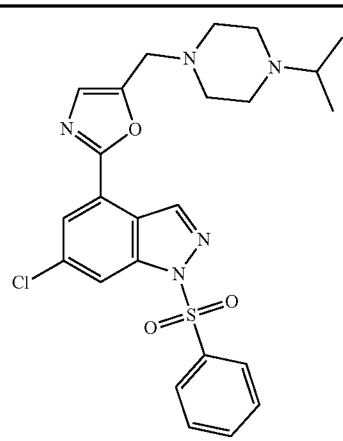 | 1-(1-methylethyl)-piperazine | 0.77 | 500 |

Intermediate 8

N-[2-(Methyloxy)-5-(4,4,5,5-tetramethyl-1,3,2-dioxaborolan-2-yl)-3-pyridinyl]methanesulfonamide

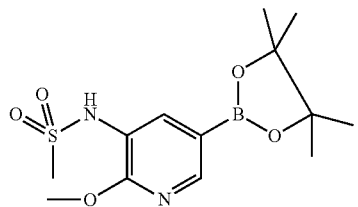 [SMILES: COc1ncc(B2OC(C)(C)C(C)(C)O2)cc1NS(C)(=O)=O]

To a solution of 2-(methyloxy)-5-(4,4,5,5-tetramethyl-1,3,2-dioxaborolan-2-yl)-3-pyridinamine (0.5 g, 1.999 mmol) in pyridine (5 ml) was added methanesulphonyl chloride (0.309 ml, 4.00 mmol) and the mixture stirred at 20° C. for 18 hr then the solvent was removed in vacuo. The residue was partitioned between saturated sodium bicarbonate solution (10 ml) and dichloromethane (20 ml), separated by hydrophobic frit and purified by silica gel chromatography, eluting with a gradient of dichloromethane and methanol to give the title compound as a brown solid (0.46 g).

LCMS (Method A): Rt 0.98 mins, MH+ 329.

Intermediate 9

2,4-Difluoro-N-[2-(methyloxy)-5-(4,4,5,5-tetramethyl-1,3,2-dioxaborolan-2-yl)-3-pyridinyl]benzenesulfonamide

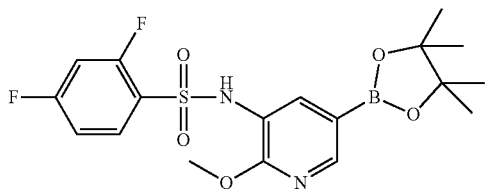 [SMILES: COc1ncc(B2OC(C)(C)C(C)(C)O2)cc1NS(=O)(=O)c1ccc(F)cc1F]

To a stirred solution of 2-(methyloxy)-5-(4,4,5,5-tetramethyl-1,3,2-dioxaborolan-2-yl)-3-pyridinamine (3 g, 12.00 mmol) in pyridine (12 ml), 2,4-difluorobenzenesulfonyl chloride (1.774 ml, 13.19 mmol) was added and the reaction mixture stirred at RT for 2 h. 2 N hydrogen chloride (aq) (20 ml) and dichloromethane (20 ml) were added and the layers separated. The aqueous layer was washed with additional dichloromethane (2×15 ml) and the organic layers combined, dried (hydrophobic frit) and evaporated in vacuo to give a brown oil. There was still some pyridine in the reaction mixture so 2M hydrogen chloride (aq) and dichloromethane (15 ml) were added to extract one more time. The solvent was removed in vacuo to give the title compound as an orange solid (4.3 g).

LCMS (Method A): Rt 1.20 min, MH+ 427 [NB. also observe Rt 0.73 min, MH+ 345 consistent with boronic acid (hydrolysis product due to HPLC eluent)].

Intermediate 10

N-[5-[4-(5-{[(2R,6S)-2,6-Dimethyl-4-morpholinyl]methyl}-1,3-oxazol-2-yl)-1-(phenylsulfonyl)-1H-indazol-6-yl]-2-(methyloxy)-3-pyridinyl]-2,4-difluorobenzenesulfonamide

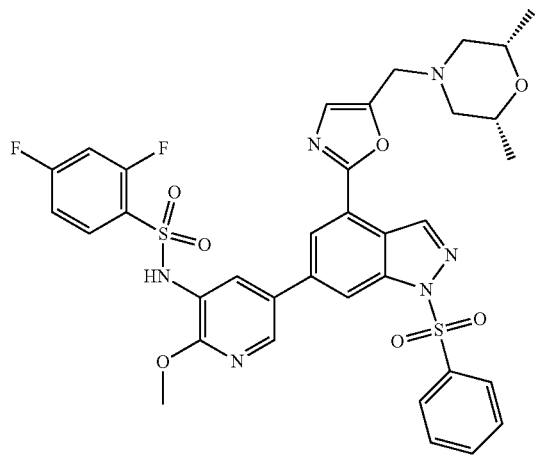 [SMILES: COc1ncc(-c2cc(-c3ncc(CN4C[C@@H](C)O[C@@H](C)C4)o3)c3cnn(S(=O)(=O)c4ccccc4)c3c2)cc1NS(=O)(=O)c1ccc(F)cc1F]

To a solution of 6-chloro-4-(5-{[(2R,6S)-2,6-dimethyl-4-morpholinyl]methyl}-1,3-oxazol-2-yl)-1-(phenylsulfonyl)-1H-indazole (0.2 g, 0.411 mmol) and 2,4-difluoro-N-[2-(methoxy)-5-(4,4,5,5-tetramethyl-1,3,2-dioxaborolan-2-yl)-3-pyridinyl]benzenesulfonamide (0.228 mg, 0.534 mmol) in 1,4-dioxane (2 ml) was added chloro[2'-(dimethylamino)-2-biphenylyl]palladium-1(1R,4S)-bicyclo[2.2.1]hept-2-yl [(1S,4R)-bicyclo[2.2.1]hept-2-yl]phosphane (11.5 mg, 0.021 mmol), potassium phosphate tribasic (0.262 g, 1.23 mmol) and water (0.2 ml). The reaction mixture was heated to 120° C. with stirring for 3 h under microwave irradiation, then filtered through a silica SPE, eluting with methanol. The solvent was removed and the residue partitioned between dichloromethane (5 ml) and water (5 ml). The layers were separated and the aqueous extracted with further dichloromethane (2×2.5 ml). The combined organics were concentrated under a stream of nitrogen and the residue dissolved in DMSO and a few drops of dichloromethane (3 ml) and purified by MDAP (method A) in 3 injections. The appropriate fractions were evaporated in vacuo to give the title compound as a pale brown solid (0.105 g).

LCMS (Method A): Rt 0.93 mins, MH+ 751.

Intermediate 11

2,4-Difluoro-N-[5-[4-(5-{[4-(1-methylethyl)-1-piperazinyl]methyl}-1,3-oxazol-2-yl)-1-(phenylsulfonyl)-1H-indazol-6-yl]-2-(methyloxy)-3-pyridinypenzenesulfonamide

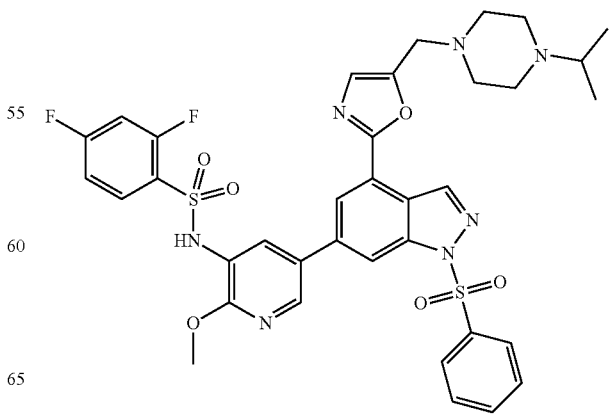

To a solution of 6-chloro-4-(5-{[4-(1-methylethyl)-1-piperazinyl]methyl}-1,3-oxazol-2-yl)-1-(phenylsulfonyl)-1H-indazole (0.2 g, 0.40 mmol) and 2,4-difluoro-N-[2-(methoxy)-5-(4,4,5,5-tetramethyl-1,3,2-dioxaborolan-2-yl)-3-pyridinyl]benzenesulfonamide (0.222 g, 0.52 mmol) in 1,4-dioxane (2 ml) was added chloro[2'-(dimethylamino)-2-biphenylyl]palladium-1(1R,4S)-bicyclo[2.2.1]hept-2-yl [(1S,4R)-bicyclo[2.2.1]hept-2-yl]phosphane (11.2 g, 0.020 mmol), potassium phosphate tribasic (0.255 g, 1.20 mmol) and water (0.2 ml). The reaction mixture was heated to 120° C. with stirring for 3 h under microwave irradiation then filtered through a silica SPE, eluting with methanol. The solvent was removed in vacuo and the residue partitioned between dichloromethane (5 ml) and water (5 ml). The layers were separated and the aqueous extracted with further dichloromethane (2×2 ml). The combined organics were concentrated under a stream of nitrogen and the residue purified using silica gel chromatography, eluting with 0-25% methanol in dichloromethane. The appropriate fractions were evaporated in vacuo to give the title compound as a brown solid (0.081 g).

LCMS (Method A): Rt 0.85 mins, MH+ 764.

Intermediate 12

Ethyl 2-[6-{1-[(1,1-dimethylethyl)(dimethyl)silyl]-1H-indol-4-yl}-1-(phenylsulfonyl)-1H-indazol-4-yl]-1,3-oxazole-5-carboxylate

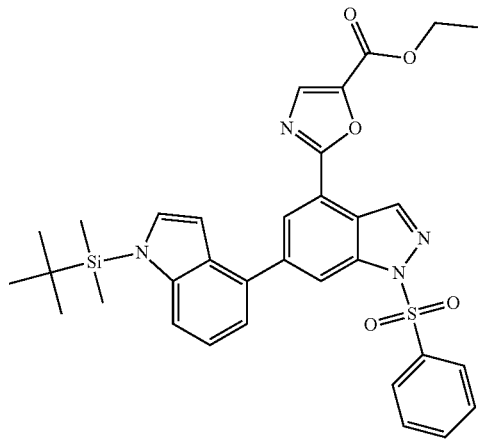 [SMILES: CCOC(=O)c1cnc(-c2cc(-c3cccc4c3ccn4[Si](C)(C)C(C)(C)C)cc3c2cnn3S(=O)(=O)c2ccccc2)o1]

To a solution of ethyl 2-[6-chloro-1-(phenylsulfonyl)-1H-indazol-4-yl]-1,3-oxazole-5-carboxylate (1.5 g, 3.47 mmol) in 1,4-dioxane (15 ml) and water (1.5 ml) was added {1-[(1,1-dimethylethyl)(dimethyl)silyl]-1H-indol-4-yl}boronic acid (1.243 g, 4.52 mmol, available from Combi-Blocks Inc.), chloro[2'-(dimethylamino)-2-biphenylyl]palladium-1(1R,4S)-bicyclo[2.2.1]hept-2-yl[(1S,4R)-bicyclo[2.2.1]hept-2-yl]phosphane (0.097 g, 0.174 mmol) and potassium phosphate tribasic (2.212 g, 10.42 mmol). The reaction mixture was heated to 100° C. for 3 h, the solvent removed in vacuo and the residue partitioned between dichloromethane (20 ml) and water (10 ml). Saturated sodium chloride solution (100 ml) was added and the organic phase separated and dried over anhydrous sodium sulphate. The crude product was purified by silica gel chromatography, eluting with a gradient of cyclohexane and ethyl acetate. The desired fractions were concentrated to give the title compound as a white solid (0.846 g), which by LCMS contained some unreacted starting material.

LCMS (Method A): Rt 1.71 mins, MH+ 627 (and Rt 1.39 min, MH+ 432 consistent with ethyl 2-[6-{1-[(1,1-dimethylethyl)(dimethyl)silyl]-1H-indol-4-yl}-1-(phenylsulfonyl)-1H-indazol-4-yl]-1,3-oxazole-5-carboxylate).

Intermediate 13

{2-[6-{1-[(1,1-Dimethylethyl)(dimethyl)silyl]-1H-indol-4-yl}-1-(phenylsulfonyl)-1H-indazol-4-yl]-1,3-oxazol-5-yl}methanol

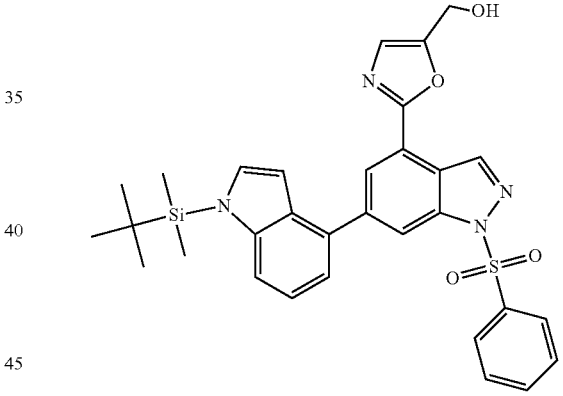

To a solution of ethyl 2-[6-{1-[(1,1-dimethylethyl)(dimethyl)silyl]-1H-indol-4-yl}-1-(phenylsulfonyl)-1H-indazol-4-yl]-1,3-oxazole-5-carboxylate (containing an impurity consistent with ethyl 2-[6-chloro-1-(phenylsulfonyl)-1H-indazol-4-yl]-1,3-oxazole-5-carboxylate)(0.84 g) in dichloromethane (10 ml) at −20° C. was added diisobutylaluminium hydride (2.68 ml, 2.68 mmol, 1M in hexanes). The reaction mixture was stirred at −20° C. for 2 h then 10% ammonium chloride solution (10 ml) added. The mixture was stirred for 5 min then extracted with dichloromethane (10 ml), the layers separated (hydrophobic frit) and the organic purified by silica gel chromatography, eluting with a gradient of cyclohexane and ethyl acetate. The desired fractions were concentrated to give the title compound as a pale yellow solid (0.36 g), which by LCMS contained an impurity consistent with 2-[6-chloro-1-(phenylsulfonyl)-1H-indazol-4-yl]-1,3-oxazol-5-yl}methanol.

LCMS (Method A): Rt 1.55 mins, MH⁺ 585 (and Rt 1.11 mins, MH⁺ 390 consistent with {2-[6-chloro-1-(phenylsulfonyl)-1H-indazol-4-yl]-1,3-oxazol-5-yl}methanol impurity).

Intermediate 14

6-Chloro-4-(5-{[(2R,6R)-2,6-dimethyl-4-morpholinyl]methyl}-1,3-oxazol-2-yl)-1-(phenylsulfonyl)-1H-indazole

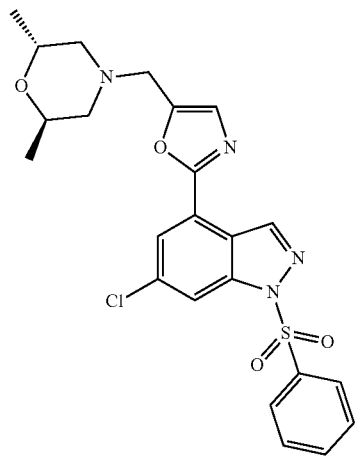 [SMILES: C[C@@H]1CN(Cc2cnc(-c3cc(Cl)cc4c3cnn4S(=O)(=O)c3ccccc3)o2)C[C@@H](C)O1]

To a solution of 4-[5-(bromomethyl)-1,3-oxazol-2-yl]-6-chloro-1-(phenylsulfonyl)-1H-indazole (750 mg, 1.657 mmol) in dichloromethane (50 mL) stirred in air at room temp, was added neat 2,6-dimethylmorpholine (191 mg, 1.657 mmol, available from Aldrich as a mixture of isomers). The reaction mixture was stirred at 20° C. for 20 hr. Volatiles were removed using a rotary evaporator then the crude material was pre-absorbed onto Fluorosil™ and purified by column chromatography on silica (100 g) using a 0-100% ethyl acetate-cyclohexane gradient over 60 mins. Two diastereoisomers were isolated. Appropriate fractions were combined and evaporated in vacuo to give the title compound as a yellow oil (226 mg).

¹H NMR confirmed the structure as the trans isomer. ¹H NMR (400 MHz, Chloroform-d) δ (ppm) 8.92 (d, J=1.0 Hz, 1H), 8.32 (dd, J=1.0, 1.5 Hz, 1H), 8.04-8.00 (m, 2H), 7.97 (d, J=1.5 Hz, 1H), 7.62 (tt, J=1.5, 7.5 Hz, 1H), 7.54-7.48 (m, 2H), 7.13 (s, 1H), 4.08-3.99 (m, J=3.5, 6.0, 6.5, 6.5, 6.5 Hz, 2H), 3.66 (d, J=14.5 Hz, 1H), 3.61 (d, J=14.5 Hz, 1H), 2.56 (dd, J=3.0, 10.5 Hz, 2H), 2.23 (dd, J=6.0, 10.5 Hz, 2H), 1.24 (d, J=6.5 Hz, 6H).

Intermediate 15

1,1-Dimethylethyl 4-({2-[6-chloro-1-(phenylsulfonyl)-1H-indazol-4-yl]-1,3-oxazol-5-yl}methyl)-1-piperazinecarboxylate

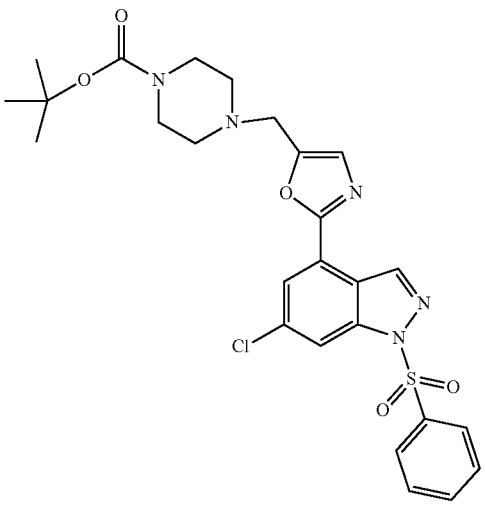 [SMILES: CC(C)(C)OC(=O)N1CCN(Cc2cnc(-c3cc(Cl)cc4c3cnn4S(=O)(=O)c3ccccc3)o2)CC1]

1,1-Dimethylethyl 1-piperazinecarboxylate (185 mg, 0.994 mmol) was dissolved in 1 ml of DCM and triethylamine (0.185 mL, 1.325 mmol) was added dropwise. The mixture was stirred for 1 h, then concentrated in vacuo to afford a yellow solid. This was dissolved in water/DCM (1:1, 50 ml) and the organic phase was collected then concentrated in vacuo to afford the title compound as a yellow gum (347 mg).

LCMS (Method A) Rt 1.16 min (poor ionisation, (M+MeCN)⁺ 599 observed).

Example 1

N-[5-[4-(5-{[(2R,6S)-2,6-Dimethyl-4-morpholinyl]methyl}-1,3-oxazol-2-yl)-1H-indazol-6-yl]-2-(methyloxy)-3-pyridinyl]methanesulfonamide

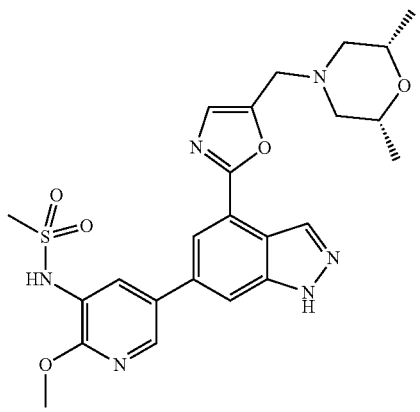

Method A

To a solution of 6-chloro-4-(5-{[(2R,6S)-2,6-dimethyl-4-morpholinyl]methyl}-1,3-oxazol-2-yl)-1-(phenylsulfonyl)-1H-indazole (0.20 g, 0.411 mmol) and N-[2-(methoxy)-5-(4,4,5,5-tetramethyl-1,3,2-dioxaborolan-2-yl)-3-pyridyl]methanesulfonamide (0.175 g, 0.534 mmol) in 1,4-dioxane (2 ml) was added chloro[2'-(dimethylamino)-2-biphenylyl]

palladium-1(1R,4S)-bicyclo[2.2.1]hept-2-yl][(1S,4R)-bicyclo[2.2.1]hept-2-yl]phosphane (11.5 mg, 0.021 mmol), potassium phosphate tribasic (0.262 g, 1.23 mmol) and water (0.2 ml). The reaction mixture was heated and stirred at 120° C. under microwave irradiation for 1 h.

Additional chloro[2'-(dimethylamino)-2-biphenylyl]palladium-1(1R,4S)-bicyclo[2.2.1]hept-2-yl][(1S,4R)-bicyclo[2.2.1]hept-2-yl]phosphane (11.5 mg, 0.021 mmol) and potassium phosphate tribasic (80 mg) were added and the reaction heated to 120° C. under microwave irradiation for 1 h. Additional potassium phospate tribasic (80 mg) was added and the reaction heated under the same conditions for a further 1h. The reaction mixture was filtered through a silica SPE and eluted with methanol. The solvent was removed in vacuo and the residue partitioned between dichloromethane (5 ml) and water (5 ml). The layers were separated and the aqueous extracted with further dichloromethane (2×2 ml). The combined organics were concentrated under a stream of nitrogen and the residue dissolved in MeOH:DMSO (3 ml, 1:1, v/v) and purified by MDAP (method A) in 3 injections. The appropriate fractions were combined and concentrated to give a white solid which was dissolved in MeOH:DMSO (1 ml, 1:1, v/v) and further purified by MDAP (method B). The appropriate fractions were basified to pH 6 with saturated sodium bicarbonate solution and extracted with ethyl acetate (2×25 ml). The combined organics were dried and evaporated in vacuo to give a white solid which was further dried under nitrogen at 40° C. for 3 h to give the title compound as a white solid (26 mg).

LCMS (Method A): Rt 0.53 mins, MH+ 513.

Method B

N-[2-(Methyloxy)-5-(4,4,5,5-tetramethyl-1,3,2-dioxaborolan-2-yl)-3-pyridinyl]methanesulfonamide (101 g, 308 mmol), 6-chloro-4-(5-{[(2R,6S)-2,6-dimethyl-4-morpholinyl]methyl}-1,3-oxazol-2-yl)-1-(phenylsulfonyl)-1H-indazole (83.3 g, 154 mmol) and sodium bicarbonate (38.8 g, 462 mmol) were suspended in 1,4-dioxane (1840 ml) and water (460 ml) under nitrogen and heated to 80° C. Chloro[2'-(dimethylamino)-2-biphenylyl]palladium-1(1R,4S)-bicyclo[2.2.1]hept-2-yl][(1S,4R)-bicyclo[2.2.1]hept-2-yl]phosphane (8.63 g, 15.40 mmol) was added and the mixture stirred overnight at 80° C.

The reaction mixture was cooled to 45° C., sodium hydroxide 2M aq. (770 ml, 1540 mmol) added and the reaction heated to 45° C. for 4 hours. The mixture was cooled to RT and diluted with water (610 mL). Dichloromethane (920 mL) was added, and the mixture was filtered twice through Celite (washed with 200 mL 1,4-dioxane/DCM 2:1 each time). The phases were separated, and aqueous washed with 1,4-dioxane/DCM 2:1 (500 mL). The aqueous phase was neutralised with hydrochloric acid to pH ~7 and extracted with 1,4-dioxane/DCM 2:1 (1 L), then 1,4 dioxane/DCM 1:1 (2×500 mL). The organics were washed with brine (500 mL), and filtered through Celite (washed with 200 mL 1,4 dioxane/DCM 2:1), and evaporated to yield a dark black solid, which was purified in 4 batches:

Batch 1: 28 g was dissolved in Toluene/Ethanol/Ammonia 80:20:2 (100 mL) and purified by column chromatography (1.5 kg silica column), eluting with Toluene/Ethanol/Ammonia 80:20:2 to give the title compound as an off-white solid (14.78 g).

Batch 2: 30 g was dissolved in methanol and mixed with Fluorisil. The solvent was then removed by evaporation and the solid purified by column chromatography (1.5 kg silica column, solid sample injection module), eluting with Toluene/Ethanol/Ammonia 80:20:2 to give the title compound as an off-white solid (9.44 g).

Batch 3: 31 g was dissolved in Toluene/Ethanol/Ammonia 80:20:2 (100 mL) and purified by column chromatography (1.5 kg silica column), eluting with Toluene/Ethanol/Ammonia 80:20:2 to give the title compound as an off-white solid (17 g).

Batch 4: 29 g was dissolved in Toluene/Ethanol/Ammonia 80:20:2 (100 mL) and purified by column chromatography (1.5 kg silica column), eluting with Toluene/Ethanol/Ammonia 80:20:2 to give the title compound as an off-white solid (21 g).

The mixed fractions from the 4 columns were combined and evaporated to yield 19 g which was dissolved in 200 mL of Toluene/Ethanol/Ammonia 80:20:2 (+ additional 4 ml of 0.88 NH3 to help solubility) then purified by column chromatography (1.5 kg silica column), eluting with Toluene/Ethanol/Ammonia 80:20:2 to give the title compound as an off-white solid (6.1 g).

All pure batches were combined (68 g) and recrystallised from ethanol (1200 mL). The suspension was heated to reflux and a solution formed. The resulting solution was then cooled to room temperature overnight. The resulting solid was then collected by filtration, washed sparingly with ethanol and dried under vacuum to give the title compound as an off-white solid (56 g). This material was recrystallised again from ethanol (1100 mL). The suspension was heated to reflux and a solution formed. The resulting solution was then cooled to room temperature overnight with stirring. The resulting solid was collected by filtration and washed sparingly with ethanol. The solid was dried in vacuo at 60° C. for 5 hrs to give the title compound as an off-white solid (45.51 g).

LCMS (Method A): Rt 0.61 mins, MH+ 513.

The filtrate from the two recrystallisations was evaporated to yield ~23 g of a solid residue that was dissolved in 200 mL of Toluene/Ethanol/Ammonia 80:20:2 (+ additional 4 ml of 0.88 NH3 to help solubility) then purified by column chromatography (1.5 kg silica column), eluting with Toluene/Ethanol/Ammonia 80:20:2 to give a further crop of the title compound as an off-white solid (18.5 g). This solid was then recrystallised from ethanol (370 mL). The suspension was heated to reflux then the resulting solution stirred for 20 mins before being allowed to cool to room temperature naturally overnight. The solid was then dried in vacuo at 65° C. overnight to give the title compound as an off-white solid (11.90 g).

LCMS (Method A): Rt 0.62 mins, MH+ 513.

Example 2

N-[5-[4-(5-{[4-(1-Methylethyl)-1-piperazinyl]methyl}-1,3-oxazol-2-yl)-1H-indazol-6-yl]-2-(methyloxy)-3-pyridinyl]methanesulfonamide

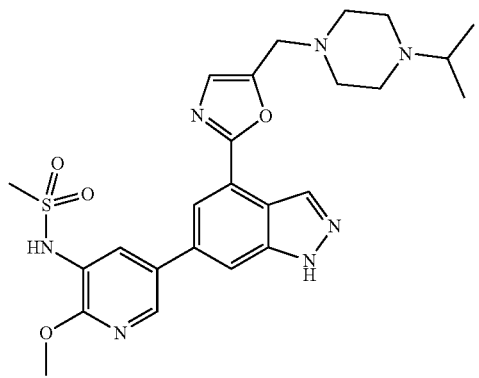 [SMILES: COc1ncc(-c2cc(-c3ncc(CN4CCN(C(C)C)CC4)o3)c3cn[nH]c3c2)cc1NS(C)(=O)=O]

To a solution of 6-chloro-4-(5-{[4-(1-methylethyl)-1-piperazinyl]methyl}-1,3-oxazol-2-yl)-1-(phenylsulfonyl)-1H-indazole (200 mg, 0.400 mmol) and N-[2-(methoxy)-5-(4,4,5,5-tetramethyl-1,3,2-dioxaborolan-2-yl)-3-pyridyl]methanesulfonamide (171 mg, 0.520 mmol) in 1,4-dioxane (2 ml) was added chloro[2'-(dimethylamino)-2-biphenylyl]palladium-1(1R,4S)-bicyclo[2.2.1]hept-2-yl[(1S,4R)-bicyclo[2.2.1]hept-2-yl]phosphane (11.2 mg, 0.020 mmol), potassium phosphate tribasic (255 mg, 1.20 mmol) and water (0.2 ml). The reaction mixture was heated and stirred at 120° C. under microwave irradiation for 3 h. The reaction mixture was filtered through a silica SPE and eluted with methanol. The solvent was removed in vacuo and the residue partitioned between dichloromethane (5 ml) and water (5 ml). The layers were separated and the aqueous extracted with further dichloromethane (2×2 ml). The combined organics were concentrated under a stream of nitrogen and the residue dissolved in MeOH:DMSO (2 ml, 1:1, v/v) and purified by MDAP (method A) in 2 injections. The appropriate fractions were combined and concentrated and the residue dissolved in MeOH:DMSO (1 ml, 1:1, v/v) and further purified by MDAP (method B). The appropriate fractions were basified to pH 7 with saturated sodium bicarbonate solution and extracted with dichloromethane (2×20 ml). The combined organics were dried (hydrophobic frit) and concentrated to give the title compound as a white solid (22 mg).

LCMS (Method A): Rt 0.51 mins, MH+ 526.

Example 3

N-[5-[4-(5-({[(2R,6S)-2,6-Dimethyl-4-morpholinyl]methyl}-1,3-oxazol-2-yl)-1H-indazol-6-yl]-2-(methyloxy)-3-pyridinyl]-2,4-difluorobenzenesulfonamide

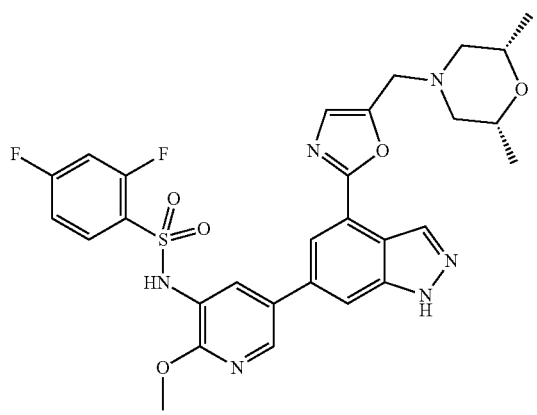 [SMILES: COc1ncc(-c2cc(-c3ncc(CN4C[C@@H](C)O[C@@H](C)C4)o3)c3cn[nH]c3c2)cc1NS(=O)(=O)c1ccc(F)cc1F]

N-[5-[4-(5-{[(2R,6S)-2,6-dimethyl-4-morpholinyl]methyl}-1,3-oxazol-2-yl)-1-(phenylsulfonyl)-1H-indazol-6-yl]-2-(methyloxy)-3-pyridinyl]-2,4-difluorobenzenesulfonamide (105 mg, 0.140 mmol) was suspended in isopropanol (2 ml) and 2M sodium hydroxide (aq) (0.699 ml, 1.399 mmol) added. The reaction mixture was stirred at RT for 2 h, the solvent removed under a stream of nitrogen and the residue dissolved in water (1 ml) and acidified to pH-6 by the addition of 2M hydrogen chloride (aq)(a black precipitate formed). The suspension was extracted with dichloromethane (3×2 ml) and the combined organics dried to give a brown solid. This was combined with the black precipitate which remained insoluble in the extraction, dissolved in MeOH:DMSO (1 ml, 1:1, v/v) and purified by MDAP (method A). The appropriate fractions were concentrated in vacuo to give the title compound as a white solid (20 mg).

LCMS (Method A): Rt 0.69 mins, MH+ 611.

Example 4

2,4-Difluoro-N-[5-[4-(5-{[4-(1-methylethyl)-1-piperazinyl]methyl}-1,3-oxazol-2-yl)-1H-indazol-6-yl]-2-(methyloxy)-3-pyridinyl]benzenesulfonamide

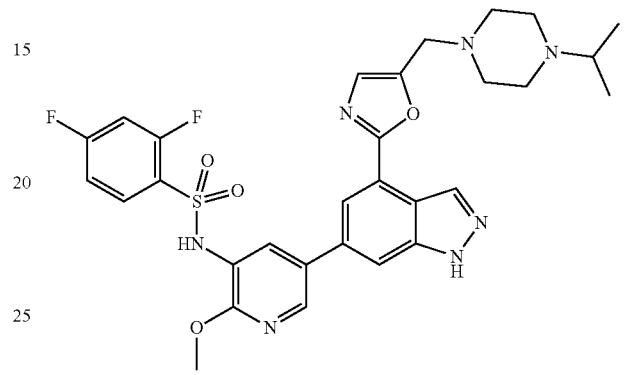

2,4-Difluoro-N-[5-[4-(5-{[4-(1-methylethyl)-1-piperazinyl]methyl}-1,3-oxazol-2-yl)-1-(phenylsulfonyl)-1H-indazol-6-yl]-2-(methyloxy)-3-pyridinyl]benzenesulfonamide (81 mg, 0.106 mmol) was suspended in isopropanol (2 ml) and 2M sodium hydroxide (aq) (0.53 ml, 1.060 mmol) was added. The reaction mixture was stirred at RT for 2 h, the solvent removed and the residue dissolved in water (1 ml) and acidified to pH-6 by the addition of 2M hydrogen chloride (aq). The resultant suspension was extracted with dichloromethane (3×2 ml), the organic layer separated (hydrophobic frit) and concentrated in vacuo to give a brown solid which dissolved in MeOH:DMSO (1 ml, 1:1, v/v) and purified by MDAP (method A). The appropriate fractions were concentrated in vacuo to give the title compound as a white solid (45 mg).

LCMS (Method A): Rt 0.65 mins, MH+ 624.

Example 5

4-(5-{[(2R,6S)-2,6-Dimethyl-4-morpholinyl]methyl}-1,3-oxazol-2-yl)-6-(1H-indol-4-yl)-1H-indazole

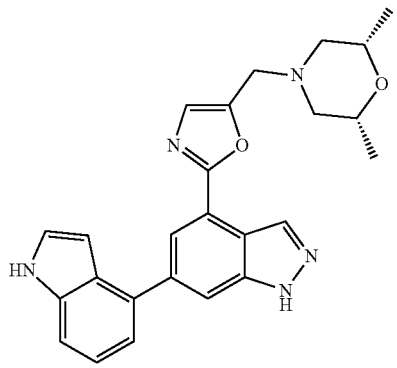 [SMILES: C[C@@H]1CN(Cc2cnc(-c3cc(-c4cccc5[nH]ccc45)cc4[nH]ncc34)o2)C[C@H](C)O1]

To a solution of 6-chloro-4-(5-{[(2R,6S)-2,6-dimethyl-4-morpholinyl]methyl}-1,3-oxazol-2-yl)-1-(phenylsulfonyl)-1H-indazole (50 mg, 0.103 mmol) in 1,4-dioxane (1.5 ml) and water (0.15 ml) was added {1-[1,1,-dimethylethyl)(dimethl)silyl]1-Hindol-4-yl}boronic acid (37 mg, 0.133 mmol), chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (5.75 mg, 10.27 μmol) and potassium phosphate tribasic (65 mg, 0.308 mmol). The reaction mixture was heated under microwave irradiation at 100° C. for 40 min. The solvent was removed and the residue dissolved in 10% methanol in dichloromethane (2 ml) and purified by silica gel chromatography, eluting with a gradient of cyclohexane and ethyl acetate. The appropriate fractions were concentrated to give a brown gum which was treated directly with tetra-n-butylammonium fluoride (0.2 ml, 0.2 mmol, 1M in tetrahydrofuran) and allowed to stand at 20° C. for 18 h. The solvent was removed and the residue dissolved in 1,4-dioxane (1 ml) and treated with 2M sodium hydroxide (1 ml) and allowed to stand at 20° C. for 48 h. The solvent was removed and the residue triturated with 10% methanol in dichloromethane then purified by silica gel chromatography, eluting with a gradient of dichloromethane and methanol to give a pale brown solid which was further purified by SCX SPE (1 g), eluting with 0.5M ammonia in 1,4-dioxane. The solvent was removed and the residue further purified by MDAP to give the title compound as a white solid (14 mg).

LCMS (Method A): Rt 0.70 mins, MH+ 428.

Example 6

6-(1H-Indol-4-yl)-4-(5-{[4-(1-methylethyl)-1-piperazinyl]methyl}-1,3-oxazol-2-yl)-1H-indazole

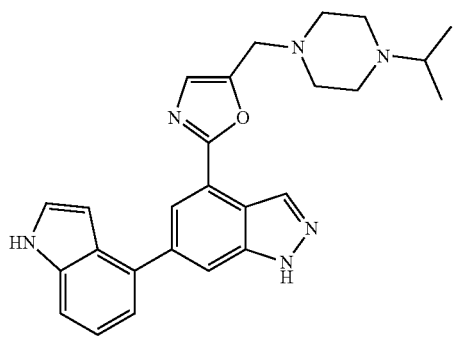 [SMILES: CC(C)N1CCN(Cc2cnc(-c3cc(-c4cccc5[nH]ccc45)cc4[nH]ncc34)o2)CC1]

Method A

6-Chloro-4-(5-{[4-(1-methylethyl)-1-piperazinyl]methyl}-1,3-oxazol-2-yl)-1-(phenylsulfonyl)-1H-indazole (97 mg, 0.194 mmol), 4-(4,4,5,5-tetramethyl-1,3,2-dioxaborolan-2-yl)-1H-indole (61.3 mg, 0.252 mmol, available from Frontier Scientific Europe), chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (10.87 mg, 0.019 mmol) and potassium phosphate tribasic (124 mg, 0.582 mmol) were dissolved in 1,4-dioxane (1 ml) and water (0.1 ml) and heated in a Biotage Initiator microwave at 100° C. for 30 min. Additional 4-(4,4,5,5-tetramethyl-1,3,2-dioxaborolan-2-yl)-1H-indole (61.3 mg, 0.252 mmol) and chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (5 mg) were added and the reaction heated at 110° C. for 30 min, then 140° C. for 30 min.

The solvent was removed in vacuo and the residue purified by silica gel chromatography, eluting with 0-25% methanol in dichloromethane. The appropriate fractions were combined and concentrated to give a brown solid which was dissolved in MeOH:DMSO (1 ml, 1:1, v/v) and purified by MDAP (method A). The appropriate fractions were concentrated in vacuo to give the title compound as a white solid (30 mg).

LCMS (Method A): Rt 0.57 mins, MH+ 441.

Method B

6-Chloro-4-(5-{[4-(1-methylethyl)-1-piperazinyl]methyl}-1,3-oxazol-2-yl)-1-(phenylsulfonyl)-1H-indazole (75.17 g, 150 mmol), 4-(4,4,5,5-tetramethyl-1,3,2-dioxaborolan-2-yl)-1H-indole (73.1 g, 301 mmol), sodium bicarbonate (37.9 g, 451 mmol), and chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (8.43 g, 15.03 mmol) were suspended in nitrogen purged 1,4-dioxane (1200 mL) and water (300 mL). The reaction vessel was placed under alternating vacuum and nitrogen five times with overhead stirring, then finally placed under a nitrogen atmosphere and heated to 120° C. for 2.5 h.

The reaction mixture was cooled to 45° C. and then treated with 2M aqueous sodium hydroxide (376 mL, 752 mmol). After stirring at 45° C. overnight (~13h), the mixture was cooled to RT and DCM (600 ml) and water (400 ml) were added. The layers were separated and the aqueous re-extracted with DCM:1,4-dioxane (1:1). Brine was added and the mixture filtered through Celite, washing with DCM:1,4-dioxane (1:1). The layers were separated and 2M HCl (1000 ml) added to the organic. The mixture was again filtered through Celite washing with 500 ml 2M HCl keeping the washings separate. The filtrate layers were then separated and the organic layer was washed with the acid washings from the Celite. Layers were separated and the acidic aqueous combined. This was then back-washed with 2×500 ml of DCM; each wash requiring a Celite filtration. The acidic aqueous was then given a final filtration through Celite washing the Celite pad with 150 ml of 2M HCl.

The acidic aqueous was transferred to a beaker (5000 ml) and with vigorous stirring 2M NaOH was added to basify the mixture to pH 10-11. The mixture was then extracted using 1,4-dioxane:DCM (1:1) (5×500 ml). The combined organics were washed with brine, dried over magnesium sulphate, filtered and evaporated to yield a brown foam that was dried in vacuo at 50° C. overnight.

This material was split into three batches and each was purified by reverse phase column chromatography (3×1.9 kg C18 column), loading in DMF/TFA (1:1, 30 ml) then eluting with 3-40% MeCN in Water+0.25% TFA (Note: Columns 2 & 3 used a different gradient starting with 10% MeCN).

Appropriate fractions were combined, the acetonitrile removed in vacuo and the acidic aqueous basified to pH10 by addition of saturated aqueous sodium carbonate solution to the stirred solution. The resultant solid was collected by filtration, washed with water then dried in vacuo at 65° C. overnight to give the title compound (28.82 g) as a pale brown foam.

LCMS (Method A): Rt 0.68 mins, MH+ 441.

$^1$H NMR (400 MHz, DMSO-d$_6$) d=13.41 (br. s., 1H), 11.35 (br. s., 1H), 8.59 (br. s., 1H), 8.07 (d, J=1.5 Hz, 1H), 7.90 (br. s., 1H), 7.51-7.44 (m, 2H), 7.32 (s, 1H), 7.27-7.21 (m, 2H), 6.61-6.58 (m, 1H), 3.73 (br. s., 2H), 2.64-2.36 (m, 9H), 0.97-0.90 (m, 6H)

Example 7

6-(1H-Indol-4-yl)-4-[5-(4-morpholinylmethyl)-1,3-oxazol-2-yl]-1H-indazole trifluoroacetate

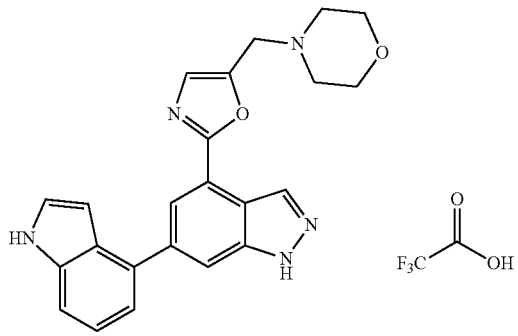 [SMILES: c1cc(-c2cc(-c3ncc(CN4CCOCC4)o3)c3cn[nH]c3c2)c2cc[nH]c2c1 ; O=C(O)C(F)(F)F]

To a solution of {2-[6-{1-[(1,1-dimethylethyl)(dimethyl)silyl]-1H-indol-4-yl}-1-(phenylsulfonyl)-1H-indazol-4-yl]-1,3-oxazol-5-yl}methanol (containing an impurity consistent with 2-[6-chloro-1-(phenylsulfonyl)-1H-indazol-4-yl]-1,3-oxazol-5-yl}methanol) (350 mg) in dichloromethane (10 ml) was added carbon tetrabromide (397 mg, 1.197 mmol). The reaction mixture was cooled to 0° C. and triphenylphosphine (314 mg, 1.197 mmol) as a solution in dichloromethane (2 ml) was added dropwise. The reaction mixture was allowed to warm to RT then the solvent partially removed and the solution purified directly by silica gel chromatography, eluting with a gradient of dichloromethane and ethyl acetate. The desired fractions were concentrated to give a brown solid (37 mg).

To a solution of the solid (30 mg, 0.056 mmol) in dichloromethane (5 ml) was added morpholine (9.8 mg, 0.112 mmol) and the mixture stirred at 20° C. for 18 h. The solvent was removed and the residue dissolved in 1,4-dioxane (2 ml) and 2M sodium hydroxide solution (1 ml, 2.0 mmol) added. The reaction mixture was stirred at 20° C. for 18 h then the solvent removed and the residue triturated with 10% methanol in dichloromethane (1 ml) and purified by silica gel chromatography, eluting with a gradient of dichloromethane and dichloromethane+1% ammonia in methanol. The desired fractions were concentrated and purified by MDAP to give the title compound as a brown solid (3 mg).

LCMS (Method A): Rt 0.65 mins, MH+ 400.

Example 8

N-[5-[4-(5-([(2R,6R)-2,6-Dimethyl-4-morpholinyl]methyl}-1,3-oxazol-2-yl)-1H-indazol-6-yl]-2-(methyloxy)-3-pyridinyl]methanesulfonamide

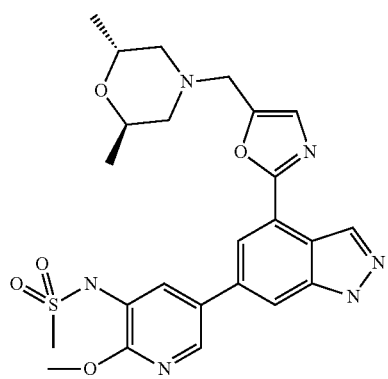 [SMILES: COc1ncc(-c2cc(-c3ncc(CN4C[C@@H](C)O[C@H](C)C4)o3)c3cn[nH]c3c2)cc1NS(C)(=O)=O]

To a solution of 6-chloro-4-(5-{[(2R,6R)-2,6-dimethyl-4-morpholinyl]methyl}-1,3-oxazol-2-yl)-1-(phenylsulfonyl)-1H-indazole (109.5 mg, 0.225 mmol), N-[2-(methyloxy)-5-(4,4,5,5-tetramethyl-1,3,2-dioxaborolan-2-yl)-3-pyridinyl]methanesulfonamide (148 mg, 0.450 mmol) and sodium bicarbonate (56.7 mg, 0.675 mmol) in 1,4-Dioxane (5 mL) and Water (1.5 mL) stirred in air at room temp was added solid Solvias Catalyst (12.60 mg, 0.022 mmol). The reaction mixture was stirred at 120° C. for 2 hr. After this time, sodium hydroxide solution (2N, 0.5 mL) was added and the reaction mixture left to stir at room temperature for two hours. On cooling, the reaction mixture was passed through a celite cartridge (10 g) and washed with ethyl acetate. The resulting solution was evaporated and the crude residue purified by MDAP (Method C). Appropriate fractions were combined and concentrated in vacuo to afford the title compound (43 mg).

LCMS (Method A) Rt 0.63 mins, MH+ 513.

Example 9

6-(1H-Indol-4-yl)-4-[5-(1-piperazinylmethyl)-1,3-oxazol-2-yl]-1H-indazole

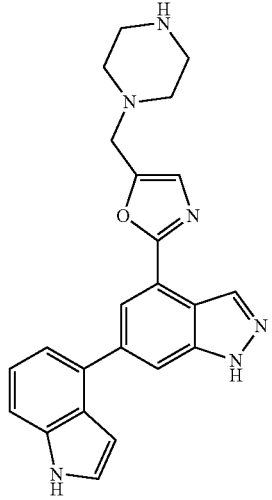 [SMILES: c1cc(-c2cc(-c3ncc(CN4CCNCC4)o3)c3cn[nH]c3c2)c2cc[nH]c2c1]

1,1-Dimethylethyl 4-({2-[6-chloro-1-(phenylsulfonyl)-1H-indazol-4-yl]-1,3-oxazol-5-yl}methyl)-1-piperazinecarboxylate (303 mg, 0.543 mmol), 4-(4,4,5,5-tetramethyl-1,3,2-dioxaborolan-2-yl)-1H-indole (172 mg, 0.706 mmol, available from Frontier Scientific), chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (1:1) (30 mg, 0.054 mmol, available from Fluka) and tripotassium phosphate (346 mg, 1.629 mmol) were dissolved in 1,4-Dioxane (10 mL) and Water (2.5 mL). The reaction vessel was sealed and heated in Biotage Initiator microwave at 150° C. for 30 min. Aqueous 2M NaOH (5 ml) was then added and the mixture stirred for 2 hours. An additional portion of aqueous 2M NaOH (3 ml) was added and stirring continued until deprotection appeared complete by LCMS analysis. DCM was then added and the mixture was passed through a phase separator. The organic phase was collected. The aqueous phase was back extracted with DCM then the organic phases were combined and evaporated to give a brown oil. This was dissolved in 5 ml of 4M HCl in 1,4 dioxane and left stirring. The mixture was concentrated in vacuo and the resultant solid partitioned between DCM and 2M aqueous HCl. The aqueous phase was basified with 2M aqueous NaOH, then washed with DCM. The organic phase was concentrated in vacuo, then the residue dissolved in 2 ml DMSO/MeOH (1:1) and purified by MDAP (Method A). Combining appropriate fractions and concentrating by blow down under nitrogen at 40° C., afforded the title compound (43 mg).

LCMS (Method A) Rt 0.62 mins, MH+ 399.

Example 10

6-(1H-Indol-4-yl)-4-(5-{[4-(1-methylethyl)-1-piperazinyl]methyl}-1,3-oxazol-2-yl)-1H-indazole hydrochloride

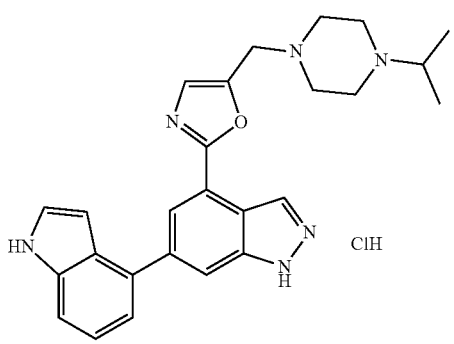

A solution of 6-(1H-indol-4-yl)-4-(5-{[4-(1-methylethyl)-1-piperazinyl]methyl}-1,3-oxazol-2-yl)-1H-indazole in tetrahydrofuran (THF) (7.5 mL) was heated to 60° C. under nitrogen. 2M hydrochloric acid in diethyl ether (0.567 mL, 1.135 mmol) and tetrahydrofuran (THF) (0.5 mL) were mixed and added via a dropping funnel. The solution was stirred at 60° C. for 30 mins before being slowly cooled to RT. After stirring at RT for a further 30 mins the solid was filtered off, then recombined with the liquors and evaporated to dryness. THF (10 mL) was added and the slurry was cycled from RT to reflux 3 times (30 mins hold at higher/low temp). The slurry was stirred at RT for one hour then filtered under vacuum and the resultant solid dried in a vacuum oven at 50° C. overnight to give the title compound as a an off-white solid (322 mg).

LCMS (Method A): Rt 0.66 mins, MH+ 441. $^1$H NMR (400 MHz, DMSO-d$_6$) d=13.53 (s, 1H), 11.44 (br. s., 1H), 10.20 (br. s., 1H), 8.61 (s, 1H), 8.08 (s, 1H), 7.92 (s, 1H), 7.52-7.46 (m, 2H), 7.41 (s, 1H), 7.28-7.19 (m, 2H), 6.60 (br. s., 1H), 3.87 (s, 2H), 3.41-3.32 (m, 3H+, obscured by H2O), 3.10-2.93 (m, 4H), 2.71-2.58 (m, 2H), 1.23 (d, J=6.5 Hz, 6H).

Example 11

6-(1H-Indol-4-yl)-4-(5-{[4-(1-methylethyl)-1-piperazinyl]methyl}-1,3-oxazol-2-yl)-1H-indazole dihydrochloride

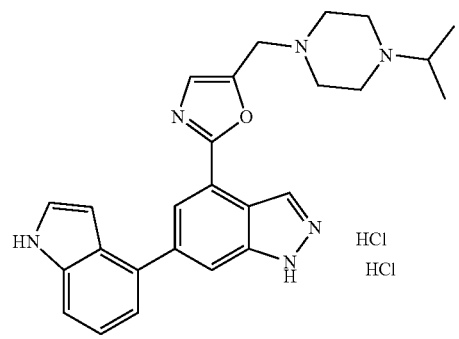 [SMILES: CC(C)N1CCN(Cc2cnc(-c3cc(-c4cccc5[nH]ccc45)cc4[nH]ncc34)o2)CC1 ; Cl ; Cl]

6-(1H-Indol-4-yl)-4-(5-{[4-(1-methylethyl)-1-piperazinyl]methyl}-1,3-oxazol-2-yl)-1H-indazole (19.4 mg, 0.044 mmol) was dissolved in tetrahydrofuran (THF) (0.5 ml) and 4M HCl in dioxane (0.022 ml, 0.088 mmol) added. The mixture was stirred at RT for 2 h, then the cream precipitate formed was filtered off and dried in a vacuum oven overnight to give the title compound as a beige solid (15.5 mg).

LCMS (Method A): Rt 0.65 mins, MH+ 441.
$^1$H NMR (600 MHz, DMSO-d$_6$) d=13.47 (br. s., 1H), 11.38 (br. s., 1H), 10.17 (br. s., 1H), 8.66 (s, 1H), 8.13 (s, 1H), 7.93 (s, 1H), 7.51 (br. s., 1H), 7.49 (dt, J=1.0, 7.5 Hz, 1H), 7.47 (t, J=3.0 Hz, 1H), 7.25 (t, J=7.0 Hz, 1H), 7.23 (dd, J=1.5, 7.0 Hz, 1H), 6.60 (ddd, J=1.0, 2.0, 3.0 Hz, 1H), 4.17 (br. s., 2H), 3.50-3.39 (m, 3H), 3.35-3.25 (m, 2H), 3.22-3.11 (m, 2H), 2.99-2.76 (m, 2H), 1.24 (d, J=6.5 Hz, 6H).

Example 12

N-5-[4-(5-{[(2R,6S)-2,6-Dimethyl-4-morpholinyl]methyl}-1,3-oxazol-2-yl)-1H-indazol-6-yl]-2-(methyloxy)-3-pyridinyl]methanesulfonamide (R)-mandelate

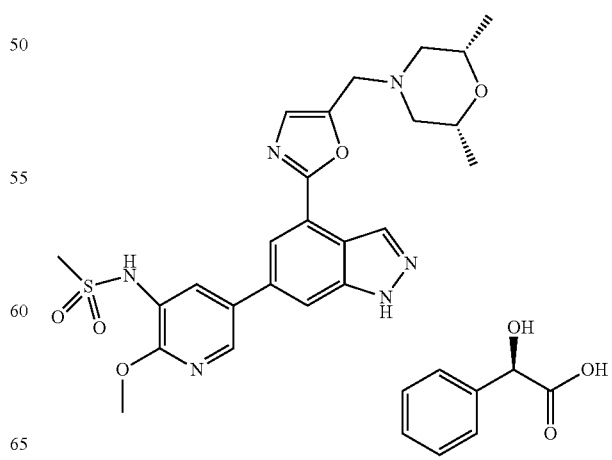

Method A

N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (113 mg, 0.220 mmol) was suspended in water (18 ml) and (R)-mandelic acid (0.33M solution in water, 735 μl, 0.242 mmol) was added. The mixture was stirred at RT overnight then concentrated and dried in a vacuum oven at 50° C. overnight to give the title compound as a white solid (133 mg).

LCMS (Method A): Rt 0.60 mins, MH+513.

$^1$H NMR (400 MHz, DMSO-$d_6$) d=13.53 (br. s., 1H), 9.43 (s, 1H), 8.58 (s, 1H), 8.43 (d, J=2.5 Hz, 1H), 7.99 (d, J=2.5 Hz, 1H), 7.93 (d, J=1.5 Hz, 1H), 7.89 (s, 1H), 7.36 (s, 1H), 7.43-7.24 (m, 5H), 5.01 (s, 1H), 3.99 (s, 3H), 3.75 (s, 2H), 3.63-3.52 (m, 2H), 3.11 (s, 3H), 2.81 (d, J=10.5 Hz, 2H), 1.78 (t, J=10.5 Hz, 2H), 1.04 (d, J=6.5 Hz, 6H).

Note—mandelate only present at a molar ratio of 0.8.

Method B

N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (3.17 mg) was suspended in 5% dextrose/water (3 ml). A 100 mg/ml aqueous solution of (R)-mandelic acid (10 μl) was added and the mixture stirred for 45 min to give the title compound as a clear solution.

Polymorph Experimental

Example 10

X-Ray Powder Diffraction (XRPD)

The data were acquired on a PANalytical X'Pert Pro powder diffractometer, model PW3040/60, serial number DY1850 using an X'Celerator detector. The acquisition conditions were: radiation: Cu Kα, generator tension: 40 kV, generator current: 45 mA, start angle: 2.0° 2θ☐, end angle: 40.0° ☐2θ, step size: 0.0167° 2θ, time per step: 31.75 seconds. The sample was prepared by mounting a few milligrams of sample on a Si wafer (zero background) plates, resulting in a thin layer of powder.

The X-ray powder diffraction (XRPD) data are shown in FIG. 1.

Characteristic peaks for the solid state form are summarised in Table 1 with calculated lattice spacings. Peak positions were measured using Highscore software.

TABLE 1

| 2θ/° | d-spacing/Å |
| --- | --- |
| 5.2 | 17.0 |
| 10.3 | 8.6 |
| 12.8 | 6.9 |
| 14.8 | 6.0 |
| 15.1 | 5.9 |
| 15.6 | 5.7 |
| 16.8 | 5.3 |
| 17.2 | 5.2 |
| 18.3 | 4.9 |
| 19.6 | 4.5 |
| 20.9 | 4.2 |
| 21.3 | 4.2 |
| 21.7 | 4.1 |
| 23.2 | 3.8 |
| 24.0 | 3.7 |
| 24.9 | 3.6 |
| 26.0 | 3.4 |
| 27.1 | 3.3 |

TABLE 1-continued

| 2θ/° | d-spacing/Å |
| --- | --- |
| 27.5 | 3.2 |
| 28.2 | 3.2 |
| 28.5 | 3.1 |

Example 1

X-Ray Powder Diffraction (XRPD)

The data were acquired using a similar method to that described above.

The X-ray powder diffraction (XRPD) data are shown in FIG. 2.

Characteristic peaks for the solid state form are summarised in Table 2 with calculated lattice spacings. Peak positions were measured using Highscore software.

TABLE 2

| 2θ/° | d-spacing/Å |
| --- | --- |
| 4.5 | 19.8 |
| 6.3 | 13.9 |
| 7.8 | 11.3 |
| 8.8 | 10.1 |
| 9.9 | 8.9 |
| 10.4 | 8.5 |
| 10.7 | 8.3 |
| 11.3 | 7.8 |
| 11.7 | 7.5 |
| 12.2 | 7.3 |
| 12.9 | 6.9 |
| 14.0 | 6.3 |
| 14.5 | 6.1 |
| 15.2 | 5.8 |
| 15.4 | 5.7 |
| 16.1 | 5.5 |
| 16.5 | 5.4 |
| 16.8 | 5.3 |
| 17.7 | 5.0 |
| 17.9 | 5.0 |
| 18.5 | 4.8 |
| 19.0 | 4.7 |
| 20.7 | 4.3 |
| 21.4 | 4.1 |
| 22.4 | 4.0 |
| 22.6 | 3.9 |
| 23.4 | 3.8 |
| 23.7 | 3.8 |
| 24.9 | 3.6 |
| 25.4 | 3.5 |
| 25.7 | 3.5 |

Biological Data

PI3K Alpha, Beta, Delta and Gamma Assays

Assay Principle

The assay readout exploits the specific and high affinity binding of PIP3 to an isolated pleckstrin homology (PH) domain in the generation of a signal. Briefly, the PIP3 product is detected by displacement of biotinylated PIP3 from an energy transfer complex consisting of Europium (Eu)-labelled anti-GST monoclonal antibody, a GST-tagged PH domain, biotin-PIP3 and Streptavidin-APC. Excitation of Eu leads to a transfer of energy to APC and a sensitized fluorescence emission at 665 nm. PIP3 formed by PI3kinase activity competes for the binding site on the PH domain, resulting in a loss of energy transfer and a decrease in signal.

Assay Protocol

Solid compounds are typically plated with 0.1 μl of 100% DMSO in all wells (except column 6 and 18) of a 384-well, v bottom, low volume Greiner plate. The compounds are serially diluted (4-fold in 100% DMSO) across the plate from column 1 to column 12 and column 13 to column 24 and leave column 6 and 18 containing only DMSO to yield 11 concentrations for each test compound.

The assays are run using specific PI3 kinase kits from Millipore (Cat#33-001) The assay kit consist of the following:

4×PI3K reaction buffer (Contains 200 mM Hepes pH 7, 600 mM NaCl, 40 mM Mgcl$_2$, <1% Cholate (w/v), <1% Chaps (w/v), 0.05% Sodium Azide (w/v))
PIP2 (1 mM)
3×Biotin PIP3 (50 μM)
Detection Mix C (Contains 267 mM KF)
Detection Mix A (Contains 60 μg/ml streptavadin-APC)
Detection Mix B (Contains 36 μg/ml Europium-anti-GST (Anti-GST-K) and 90 μg/ml GST-GRP1-PH-Domain and 1 mM DTT)
Stop Solution (Contains 150 mM EDTA)
Manually add 3 μl of Reaction buffer (contains 1 mM DTT) to column 18 only for 100% inhibition control (no activity)
Manually add 3 μl of 2× Enzyme solution to all wells except column 18. Preincubate with compound for 15 minutes.
Manually add 3 μl of 2× Substrate solution to all wells. (column 6 represents 0% inhibition control)
Leave plate for 1 hr (cover from light) (In the case of Gamma only a 50 min incubation is required)
Manually add 3 μl Stop/Detection solution to all wells
Leave plate for 1 hour (cover from light)
The assay is read upon the BMG Rubystar and the ratio data is utilised to calculate 11 point curves.

NB The substrate solution (concentrations) differ with each isoform (see below)

Alpha
2×substrate solution containing 500 μM ATP, 16 μM PIP2 and 0.030 μM 3× biotin-PIP3.

Beta
2×substrate solution containing 800 μM ATP, 16 μM PIP2 and 0.030 μM 3× biotin-PIP3.

Delta
2× substrate solution containing 160 μM ATP, 10 μM PIP2 and 0.030 μM 3× biotin-PIP3.

Gamma
2× substrate solution containing 30 μM ATP, 16 μM PIP2 and 0.030 μM 3× biotin-PIP3.

Analysis Method
Data processed through the XC50 4-parameter logistic curve fit algorithm in Activity Base.
Normalise to % inhibition between the high and low controls (0% and 100% inhibition respectively)
Primary Module fit: Slope, Min and Max asymptotes varies
Secondary Module fits: (1) Fix Min asymptote, (2) Fix Max asymptote, (3) Fix Min and Max asymptotes
Curve Fit QC: pXC50 95% CL ratio >10
−20<Min asymptote <20
80<Max asymptote <120

The compounds and salts of Examples 1 to 10 and 12 were tested in the PI3K Alpha, Beta, Delta and/or Gamma assays above or similar assays and were found to have a mean pIC$_{50}$ in the PI3K Delta assay of at least 7 or greater.

The compounds and salts of at least Examples 1, 2, 5 to 10 and 12 were found to have at least tenfold selectivity for PI3K Delta over PI3K Alpha, Beta and/or Gamma.

What is claimed is:
1. A compound of formula (I):

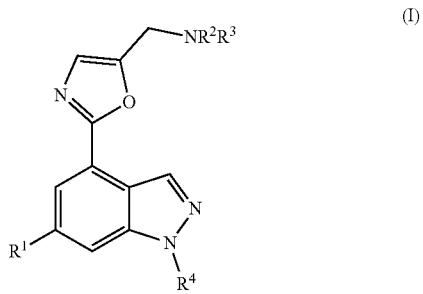

wherein
$R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo, —CN or —NHSO$_2$R$^5$, or
pyridinyl optionally substituted by one or two substituents independently selected from $C_{1-6}$alkyl, —OR$^6$, halo and —NHSO$_2$R$^7$;
$R^2$ and $R^3$, together with the nitrogen atom to which they are attached, are linked to form a 6- or 7-membered heterocyclyl wherein the 6- or 7-membered heterocyclyl optionally contains an oxygen atom or a further nitrogen atom;
$R^4$ is methyl;
$R^6$ is hydrogen or $C_{1-4}$alkyl; and
$R^5$ and $R^7$ are each independently $C_{1-6}$alkyl, or phenyl optionally substituted by one or two substituents independently selected from halo;
or a salt thereof.

2. The compound according to claim 1, wherein $R^1$ is 9-membered bicyclic heteroaryl wherein the 9-membered bicyclic heteroaryl contains one or two nitrogen atoms, or pyridinyl optionally substituted by one or two substituents independently selected from —OR$^6$ and —NHSO$_2$R$^7$.

3. A compound according to claim 1, wherein $R^1$ is indolyl.

4. A compound according to claim 1, wherein $R^1$ is pyridinyl optionally substituted by one or two substituents independently selected from —OR$^6$ and —NHSO$_2$R$^7$.

5. A compound according to claim 1, wherein $R^2$ and $R^3$, together with the nitrogen atom to which they are attached, are linked to form a 6-membered heterocyclyl wherein the 6-membered heterocyclyl optionally contains an oxygen atom or a further nitrogen atom.

6. A compound according to claim 1, wherein $R^2$ and $R^3$, together with the nitrogen atom to which they are attached, are linked to form a 6-membered heterocyclyl wherein the 6-membered heterocyclyl contains an oxygen atom.

7. A compound according to claim 1, wherein $R^2$ and $R^3$, together with the nitrogen atom to which they are attached, are linked to form a 6-membered heterocyclyl wherein the 6-membered heterocyclyl contains a further nitrogen atom.

8. A compound according to claim 1 wherein the compound of formula (I) is in the form of a pharmaceutically acceptable salt thereof.

* * * * *